US011096952B2

(12) United States Patent
Cardelli et al.

(10) Patent No.: US 11,096,952 B2
(45) Date of Patent: Aug. 24, 2021

(54) CHEMICALS AND METHODS TO PREVENT AND TREAT TGF-BETA MEDIATED ACTIVATION OF FIBROBLASTS TO REDUCE AND TREAT CANCER AND FIBROSIS

(71) Applicant: Board of Supervisors of Louisiana State University and Agricultural and Mechanical College, Baton Rouge, LA (US)

(72) Inventors: James Allen Cardelli, Shreveport, LA (US); Charles Albert Stephens, Hot Springs, AR (US); Alana Lea Gray, Shreveport, LA (US); David Thomas Coleman, Shreveport, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 0 days.

(21) Appl. No.: 16/074,566

(22) PCT Filed: Feb. 2, 2017

(86) PCT No.: PCT/US2017/016160
§ 371 (c)(1),
(2) Date: Aug. 1, 2018

(87) PCT Pub. No.: WO2017/136515
PCT Pub. Date: Aug. 10, 2017

(65) Prior Publication Data
US 2019/0038655 A1 Feb. 7, 2019

Related U.S. Application Data

(60) Provisional application No. 62/290,002, filed on Feb. 2, 2016.

(51) Int. Cl.
| | |
|---|---|
| *A61K 31/7048* | (2006.01) |
| *A61K 31/4709* | (2006.01) |
| *A61K 45/06* | (2006.01) |
| *A61P 7/04* | (2006.01) |
| *A61P 35/00* | (2006.01) |
| *A61K 31/704* | (2006.01) |
| *A61K 31/045* | (2006.01) |
| *A61K 31/4412* | (2006.01) |
| *A61K 31/496* | (2006.01) |

(52) U.S. Cl.
CPC ...... *A61K 31/7048* (2013.01); *A61K 31/4709* (2013.01); *A61K 31/704* (2013.01); *A61K 45/06* (2013.01); *A61P 7/04* (2018.01); *A61P 35/00* (2018.01); *A61K 31/045* (2013.01); *A61K 31/4412* (2013.01); *A61K 31/496* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 2008/0113042 A1* | 5/2008 | Chu | A61K 36/00 424/725 |
| 2009/0099062 A1* | 4/2009 | Lee | A61K 31/4709 514/1.1 |
| 2014/0187505 A1 | 7/2014 | Pollard | |
| 2017/0027896 A1* | 2/2017 | Dejana | A61P 13/12 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Li, X., Liu, X., Deng, R., Gao, S., Yu, H., Huang, K., . . . & Yang, C. (2020). Nintedanib Inhibits Wnt3a-Induced Myofibroblast Activation by Suppressing the Src/β-Catenin Pathway. Frontiers in pharmacology, 11, 310. (Year: 2020).*
Zou, W. J., Huang, Z., Jiang, T. P., Shen, Y. P., Zhao, A. S., Zhou, S., & Zhang, S. (2017). Pirfenidone inhibits proliferation and promotes apoptosis . . . Medical science monitor: international medical journal of experimental and clinical research, 23, 6107. (Year: 2017).*
Supplementary European Search Report issued in corresponding European Patent Application No. 17748126.4 dated Dec. 9, 2019.
Lamb et al., Antibiotics that target mitochondria effectively eradicate cancer stem cells, across multiple tumor types: Treating cancer like an infectious disease, Oncotarget, vol. 6, No. 7, Jan. 22, 2015, pp. 4569-4584.
Zhu et al., Involvement of transient receptor potential melastatin-8 (TRPM8) in methol-induced calcium entry, reactive oxygen species production and cell death in rheumatoid arthritis rat synovial fibroblasts, European Journal of Pharmacology, Jan. 15, 2014, pp. 1-9.
Choi et al., Pirfenidone inhibits transforming growth factor-β1-induced fibrogenesis by blocking nuclear translocation of Smads in human retinal pigment epithelial cell line ARPE-19, Molecular Vision, Apr. 21, 2012, pp. 1010-1020.
International Search Report Corresponding to PCT/US2017/016160 dated Apr. 17, 2017.
Written Opinion Corresponding to PCT/US2017/016160 dated Apr. 17, 2017.

(Continued)

*Primary Examiner* — Dale R Miller
(74) *Attorney, Agent, or Firm* — Holoubek Patent Law, LLC; Charles Holoubek

(57) ABSTRACT

A method of treating an activated fibroblast associated disease or pre-disease condition in a mammal comprising, administering a pharmaceutical composition including a therapeutically effective amount of a first therapeutic, wherein the first therapeutic is one of an intracellular $Ca^{2+}$ elevator, a YAP/TAZ inhibitor, both a intracellular $Ca^{2+}$ elevator and a YAP/TAZ inhibitor, or pharmacologically acceptable salts, solvates, esters, amides, clathrates, stereoisomers, enantiomers, prodrugs or analogs thereof, or a combination thereof.

8 Claims, 22 Drawing Sheets

(56) References Cited

OTHER PUBLICATIONS

Del Carlo M et al., "651 Verapamil and Pentoxifylline Inhibit TGF-BETA-Stimulated TIMP-3 Production in Peyronie's Disease Fibroblasts:Evidence of Camp- and Calcium-Dependent Signaling Crosstalk", Journal of Urology, Lippincott Williams & Wilkins, Baltimore, MD, US, vol. 183, No. 4, Apr. 1, 2010, p. e255.
Kim S H et al., "Menthol regulates TRPM8—independent processes in PC-3 prostate cancer cells", Biochimica et Biophysica Acta, Molecular Basis of Disease, Amsterdam, NL, vol. 1792, No. 1, Jan. 1, 2009, pp. 33-38.
Provisional Opinion accompanying the Partial Search Report corresponding to EP Application 17 748 126.4 dated Sep. 6, 2019.
Partial Search Report accompanying the Provisional Opinion corresponding to EP Application 17 748 126.4 dated Sep. 6, 2019.

* cited by examiner

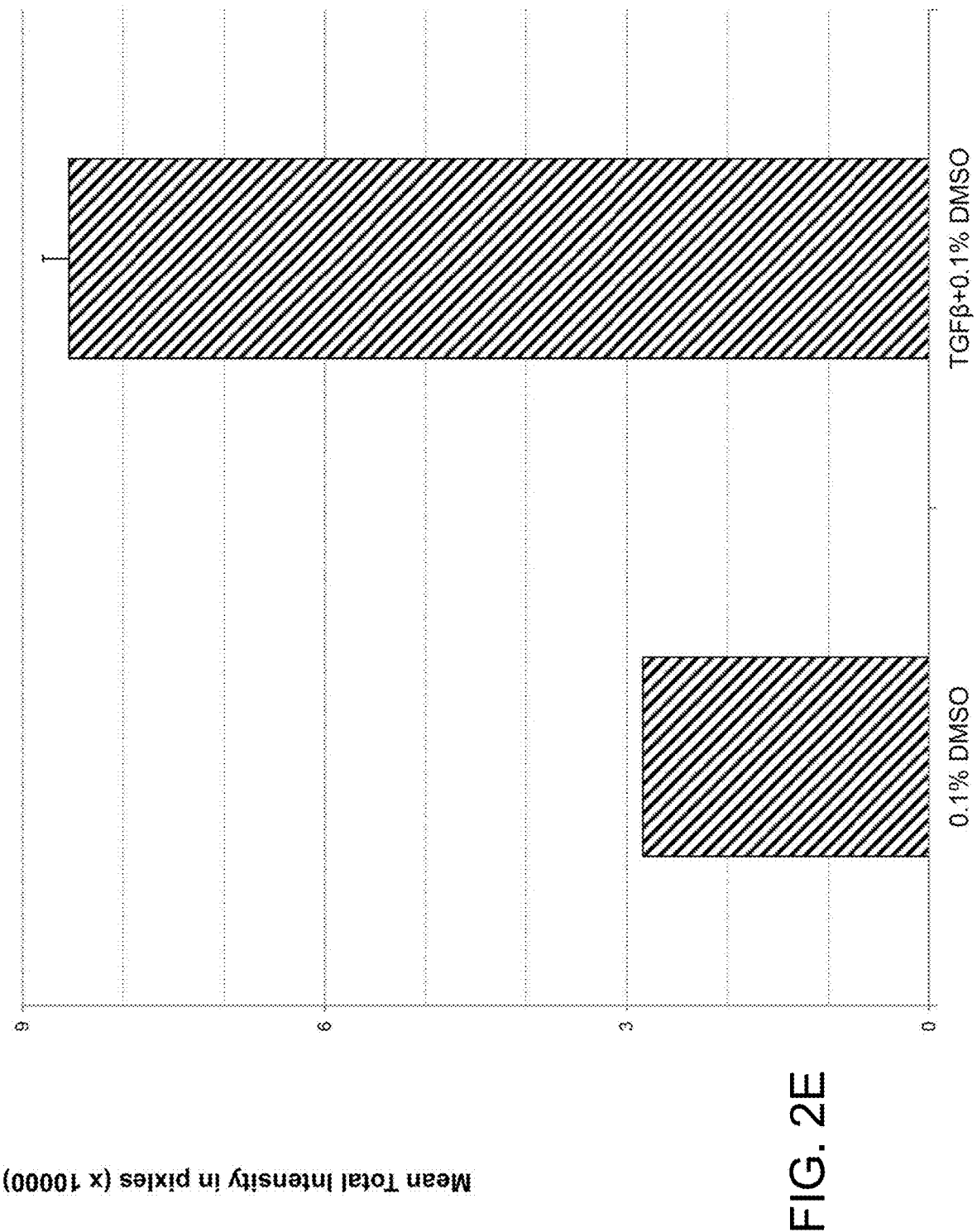

FIGS. 4A-4D
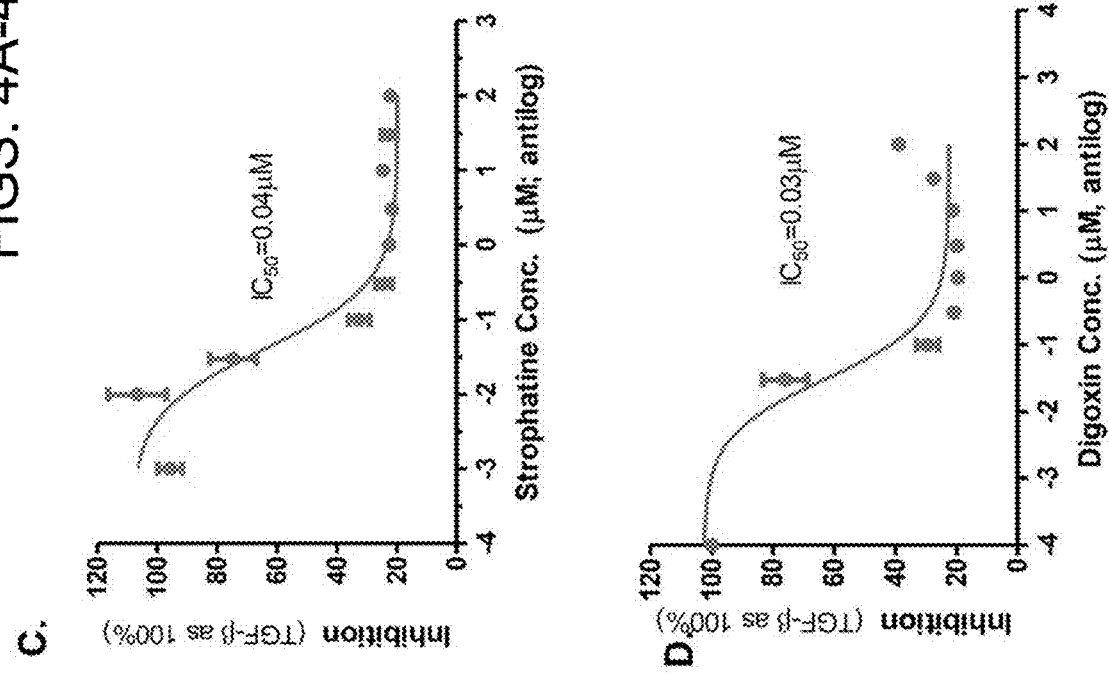
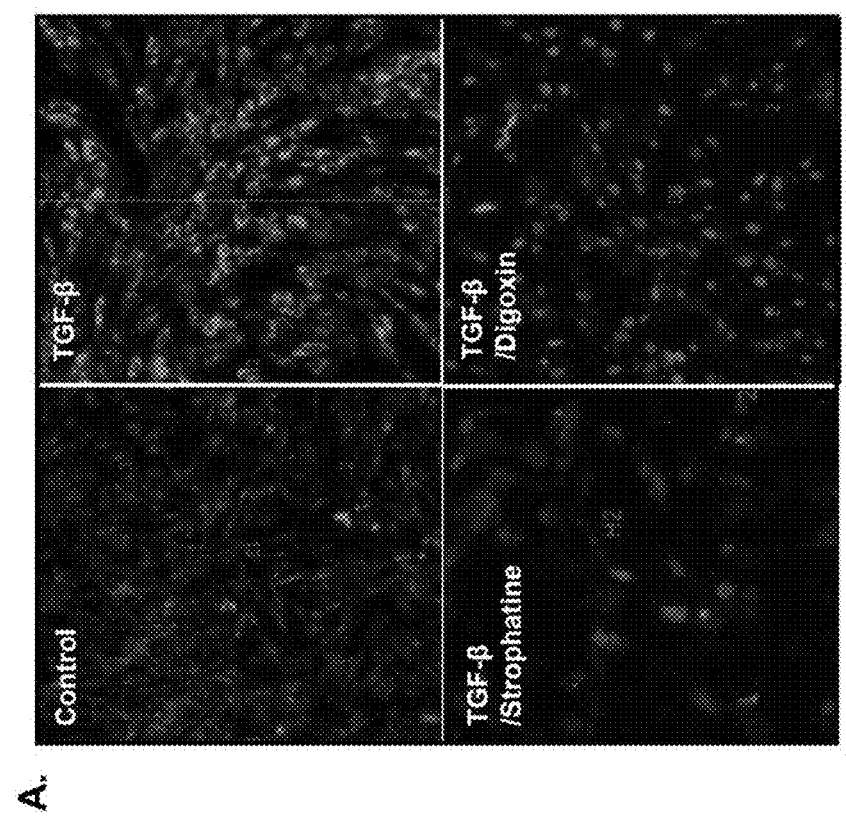

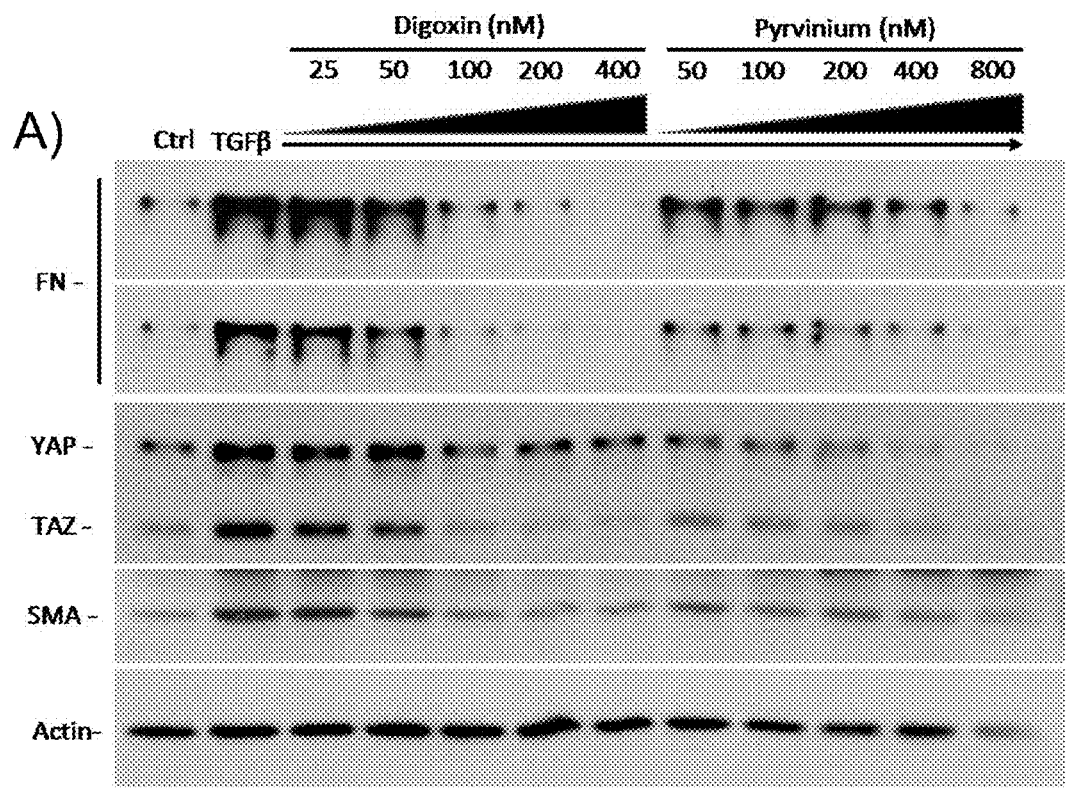
FIGS. 10A-10B
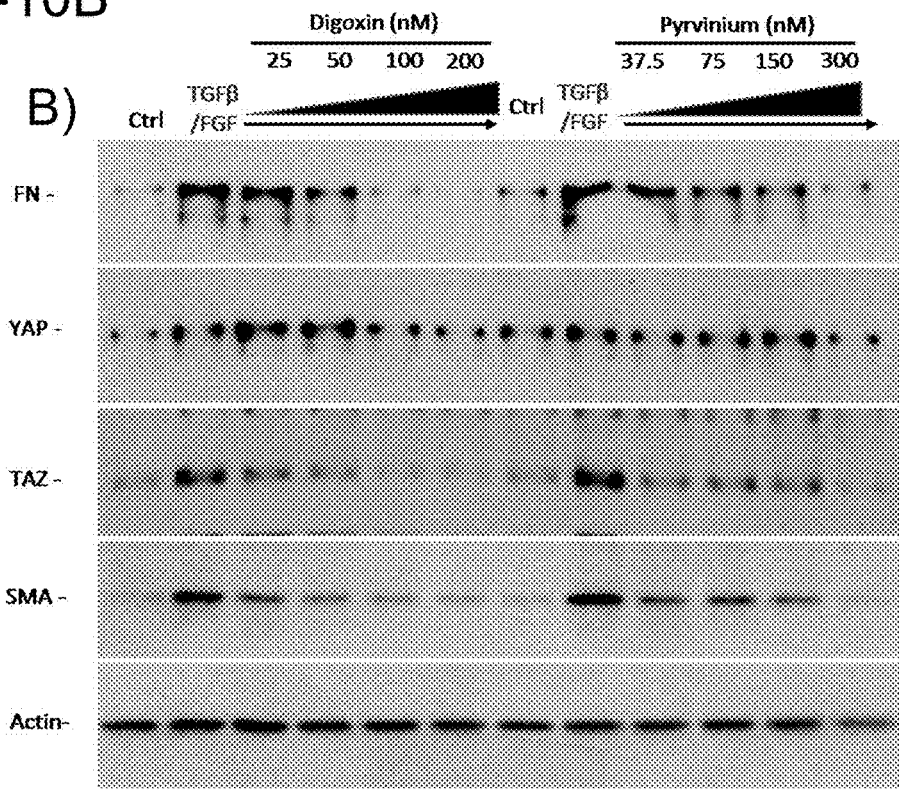

D)

| | | Digo12.5 | Digo25 | Digo50 | Digo100 | Digo200 |
|---|---|---|---|---|---|---|
| SF | 1264 | | | | | |
| TGF | 1613 | | 1496 | 1237 | 817 | 570 |
| Pyrv37.5 | | 1496 | 1377 | 1372 | 800 | |
| Pyrv75 | 1365 | 1604 | 1213 | 1005 | 1164 | |
| Pyrv150 | 1296 | 1269 | 1155 | 1020 | 963 | |
| Pyrv300 | 1244 | 1134 | 1027 | 1185 | 582 | |
| Pyrv600 | 1065 | | | | | |

E)

Table I. Prestwick Library Drugs that prevent TGF-beta induced    FIG. 14
increases in fibronection
*decrease in fibronectin*

| | plate ID | hit Name | Fibronectin ↓ | Fibronectin ↑ | know action | | | |
|---|---|---|---|---|---|---|---|---|
| | | | | | | Cardioglycoside | anti-cancer action | ↓ protein synthesis | antiparasitic |
| 1 | 6D7 | Digitoxigenin | + | | metabolic product of the cardioactive alkaloids digitoxin and gitoxin | | | |
| 2 | 6D8 | Digoxin | + | | Digoxin is used for various heart conditions | | | |
| 3 | 6H2 | Strophantine octahydrate | + | | Ouabain, also named g-strophanthin. Structurally related to digoxin. Inhibits the plasma membrane Na+/K+-ATPase. | | | |
| 4 | 9B7 | Lanatoside C | + | | Lanatoside C is a cardiac glycoside, used in the treatment of congestive heart failure and cardiac arrhythmia | | | |
| 5 | 9A7 | Helveticoside | + | | helveticoside is a cardiac glycoside | | | |
| 6 | 9G11 | Strophanthidin | + | | a cardiac glycoside | | | |
| 7 | 12A4 | Digoxigenin | + | | Cardiac glycoside. | | | |
| 8 | 13C7 | Proscillaridin A | + | | Proscillaridin is a cardiac glycoside, to treat congestive heart failure and cardiac arrhythmia. | | | |
| 9 | 6D9 | Doxorubicin hydrochloride | + | | Anthracycline family of anti-cancer medicine. works by intercalating DNA. | | | |
| 10 | 7A8 | Daunorubicin hydrochloride | + | | Anthracycline family of anti-cancer medicine | | | |
| 11 | 3D11 | Camptothecine | + | | was discovered in 1966 in screening of natural products for anticancer | | | |
| 12 | 11G7 | Azacytidine-5 | + | | 5-azacytidine is a analogue of cytidine, a nucleoside present in DNA and RNA. Azacitidine is used in the treatment of myelodysplastic syndrome. It was first synthesized as potential chemotherapeutic agents for cancer. | | | |
| 13 | 9E7 | Lycorine hydrochloride | + | | Lycorine is a toxic crystalline alkaloid. It inhibits protein synthesis (controversial) | | | |
| 14 | 10G11 | Cycloheximide | + | | Protein synthesis inhibitor | | | |
| 15 | 9G6 | Methyl benzethonium chloride | + | | Antimicrobial | | | |
| 16 | 2H7 | Ivermectin | + | | Broad-spectrum antiparasitic medicine | | | |
| 17 | 8A11 | Emetine dihydrochloride | + | | Emetine is a drug used as both an anti-protozoal and to induce vomiting. Also know as protein synthesis inhibitor. | | | |
| 18 | 13H11 | Pyrvinium pamoate | + | | Pyrvinium is an anthelmintic, only effective for pinworms.  YAP / TAK | | | |
| 19 | 2H3 | Oleandomycin phosphate | + | | Oleandomycin is a macrolide antibiotic | | | |

FIG. 15

NIH Clinical Collection Drugs that prevent TGF-beta induced increases in fibronection

| Plate ID | Name | Known Action |
| --- | --- | --- |
| 3A4 | Topotecan | Anthracycline antibiotic |
| 6B3 | Irinotecan | Anthracycline antibiotic |
| 6G3 | Etoposide | Anthracycline antibiotic |
| 2H8 | Idarubicin | Diterpenoid Epoxide and Chinese Medicine |
| 3A10 | Doxorubicin | Topoisomerase inhibitor |
| 3H6 | Epirubicin | Topoisomerase inhibitor |
| 3G7 | Triptolide | Chinese medicine |
| 6C7 | Nonyloxytrytamin | Tryptamins |
| 6G4 | Amdiodarone | Antiarrhythmic |

Table II

CHEMICALS AND METHODS TO PREVENT AND TREAT TGF-BETA MEDIATED ACTIVATION OF FIBROBLASTS TO REDUCE AND TREAT CANCER AND FIBROSIS

CROSS REFERENCE TO RELATED APPLICATIONS/PRIORITY

The application is a National Stage completion of PCT/US2017/016160 filed Feb. 2, 2017, which claims priority to U.S. Provisional Patent Application No. 62/290,002 filed Feb. 2, 2016, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

FIELD OF THE INVENTION

This invention generally relates to the screen and identification of drugs and use of these drugs for the treatment of invasive cancer and fibrotic diseases, and treatments for activated fibroblast associated diseases, including, but not limited to, treatments that target cancer associated fibroblasts.

BACKGROUND OF THE INVENTION

Fibroblasts play an important role in the development and progression of tumors as well as in fibrotic diseases such as pulmonary fibrosis, scleroderma, chronic kidney disease, and at least some cancers, just for example. Current medications to treat activated fibroblast associated diseases are inadequate in efficacy and some are toxic to the patient. In one example, tumor progression is accompanied by the activation of stromal fibroblasts into myofibroblasts often termed cancer-associated fibroblasts (CAFs). CAFs can induce invasion of tumor cells leading to metastasis. Inhibition of CAFs combined with therapies that target tumors is believed to advance cancer treatments by, in the least, preventing the CAF induced invasion of tumor cells leading to metastasis. There are currently no treatments targeting CAF differentiation, which is an attractive target for inhibiting the synthesis of multiple cancer-promoting growth factors, cytokines, proteases, and ECM components. Further, there is a separate, independent, and pressing need for treatments for both cancer activated fibroblast associated diseases or pre-disease conditions and non-cancer activated fibroblast associated diseases or pre-disease conditions.

SUMMARY OF THE INVENTION

Wherefore, it is an object of the present invention to overcome the above mentioned shortcomings and drawbacks associated with the prior art.

Tumor cells progress to invasion and metastasis in part due to communication with cells known as CAFs. This is especially prevalent in cancers such as pancreatic cancer where the five year survival rate is less than 5 percent. No accepted therapies are available that target these stromal cells. Another target is fibrotic diseases of the lung, kidney and other organs are due to over activated fibroblasts. Presently only two recent drugs with unknown long term effects therapeutic options are available for such fibrotic diseases. To identify compounds able to prevent CAF differentiation, the inventors utilized a high content imaging approach to screen the Prestwick repurposed drug library containing 1280 drugs. This screen yielded 19 drugs that blocked induction of fibronectin, a marker for CAFs. Almost one half of the 19 identified compounds belonged to the cardiac glycoside class. The inventors also screened the NIH Clinical Collection library containing over 450 compounds that have been safely used in clinical trials. The inventors present data below demonstrating that digoxin, one of these cardiac glycosides, is able to inhibit Transforming Growth Factor Beta 1 (TGF-β)-induced fibronectin extra domain A (fibronectin) production as well as CAF differentiation in vitro. Overall, these data implicate digoxin, and the other 18 repurposed drugs identified as a potential therapeutic agent that target CAFs by inhibiting their activation. Theoretically, these agents could be used alone or in combination with other standard treatments to increase anti-tumor efficacy in vivo.

The invention further relates to methods and therapeutic products including a first pharmaceutically active agent being one of an intracellular $Ca^{2+}$ elevator, including cardiac glycosides, a YAP/TAZ inhibitor, and/or a chemical listed in Tables 1 and 2, and a pharmacologically acceptable salt, solvate, ester, amide, clathrate, stereoisomer, enantiomer, prodrug or analog thereof, or a combination thereof; and a further pharmaceutically active agent.

In further embodiments the further pharmaceutically active agent is one or more additional intracellular $Ca^{2+}$ elevators, including cardiac glycosides, YAP/TAZ inhibitors, and/or chemicals listed in Tables 1 and 2, or a pharmacologically acceptable salt, solvate, ester, amide, clathrate, stereoisomer, enantiomer, prodrug or analog thereof, distinct from the first pharmaceutically active agent. In further embodiments the further pharmaceutically active agent is one or more receptor tyrosine kinase inhibitors; a receptor tyrosine kinase inhibited is one of c-Met, RON, ROS, EGFR1, EGFR2, EGFR3, EGFR4, EGRFvIII, c-Kit, c-FMS, FLT3, PDGFR, IGFR, VEGFR, VEGR2, TIE-1, TIE-2, PTK-7, FGFR1-3, TRKA-C, RORs, BCR-ABL, EPHA1-5, EPHB1-4, and RET; and the receptor tyrosine kinase inhibitor is one of Alectinib, Axitinib, Crizotinib, Cabozantinib, Centinib, Erlotinib, Gefitinib, Lapatinib, Lenvatinib, Osimertinib, Pazopanib, Ponatinib, Regorafenib, Sorafenib, Sunitinib, Tofacitinib, Vandetanib, and Vismodegib. In further embodiments the further pharmaceutically active agent is one or more agents that target non-receptor tyrosine kinases; the non-receptor tyrosine kinase is one of ABL1-2, ACK1, ELK, Bmx, bRAF, BRK, BTK, CSK, FAK, FES, FRK, FYNA, HCK, ITK, Jak1-2, LCK, Lok1, LRRK2, LYNA-B, MNK1, MEK, mTOR, PI3K, PYK2, Src, Syk, Zap-70, and CDK4; and the agent that targets the non-receptor tyrosine kinase is one of Bosultinib, Cobimetinib, Dabrafenib, Dasatinib, Everolimus, Ibrutinib, Idelalisib, Imatinib, nilotinib, Palbociclib, Ponatinib, Rogorafenib, Ruxolitinib, Temstrolimus, and Trametinib. In further embodiments the further pharmaceutically active agent is one or more anti-cell proliferative chemotherapeutic agent and the anti-cell proliferative chemotherapeutic agent is one of an anti-cancer and anti-tumor drug; an alkylating agent, anti-metabolite, plant extract, plant alkaloid, nitrosourea, hormone, nucleoside analog, and nucleotide analog; and 5-fluorouracil, cyclophospharnide, azathioprine, cyclosporin A, prednisolone, melphalan, chlorambucil, mechlorethamine, busulphan, methotrexate, 6-mercaptopurine, thioguanine, cytosine arabinoside, AZT, 5-azacytidine (5-AZC), bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, taxol (paclitaxel), Nab-paclitaxel, vinblastine, vincristine, doxorubicin, dibromomannitol, irinotecan, topotecan, etoposide, teniposide, or pemetrexed.

As used herein, the term "active agent" includes an intracellular $Ca^{2+}$ elevator, including cardiac glycosides, a YAP/TAZ inhibitor, and/or a chemical listed in Tables 1 and 2 as described herein. The term active agent may also be referred to as the active compound, active ingredient, active material, the inventive compound and/or the active drug substance.

As used herein, the term "delayed release" includes a pharmaceutical preparation, e.g., an orally administered formulation, which passes through the stomach substantially intact and dissolves in the small and/or large intestine (e.g., the colon). In some embodiments, delayed release of the active results from the use of an enteric coating of an oral medication (e.g., an oral dosage form).

The term an "effective amount" of an agent, as used herein, includes that amount sufficient to effect beneficial or desired results, such as clinical results, and, as such, an "effective amount" depends upon the context in which it is being applied.

The terms "extended release" or "sustained release" interchangeably includes a drug formulation that provides for gradual release of a drug over an extended period of time, e.g., 6-12 hours or more, compared to an immediate release formulation of the same drug. Preferably, although not necessarily, extended release results in substantially constant blood levels of a drug over an extended time period that are within therapeutic levels and fall within a peak plasma concentration range that is between, for example, 0.05-10 µM, 0.1-10 µM, 0.1-5.0 µM, or 0.1-1 ∞M.

As used herein, the terms "formulated for enteric release" and "enteric formulation" include pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

The term "immediate release," as used herein, includes that the agent (e.g., an intracellular $Ca^{2+}$ elevator, including cardiac glycosides, a YAP/TAZ inhibitor, and/or a chemical listed in Tables 1 and 2, or any pharmacologically acceptable salt, solvate, ester, amide, clathrate, stereoisomer, enantiomer, prodrug, or analog thereof, or a combination thereof), as formulated in a unit dosage form, has a dissolution release profile under in vitro conditions in which at least 55%, 65%, 75%, 85%, or 95% of the agent is released within the first two hours of administration to, e.g., a human. Desirably, the agent formulated in a unit dosage has a dissolution release profile under in vitro conditions in which at least 50%, 65%, 75%, 85%, 90%, or 95% of the agent is released within the first 30 minutes, 45 minutes, or 60 minutes of administration.

The term "pharmaceutical composition," as used herein, includes a composition containing an active agent described herein (e.g., an intracellular $Ca^{2+}$ elevator, including cardiac glycosides, a YAP/TAZ inhibitor, and/or a chemical listed in Tables 1 and 2, or any pharmacologically acceptable salt, solvate, ester, amide, clathrate, stereoisomer, enantiomer, prodrug, or analog thereof, or a combination thereof), formulated with a pharmaceutically acceptable excipient, and typically manufactured or sold with the approval of a governmental regulatory agency as part of a therapeutic regimen for the treatment of disease in a mammal, especially with the mammal being a human. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, includes an ingredient other than the active agents described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, includes those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, includes those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetrarnethylamrnonium, tetraethylammonium, methylamine, dimethylamine, trimethylamine, triethylamine, ethylarnine, and the like.

The terms "pharmaceutically acceptable solvate" or "solvate," as used herein, includes a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and trihydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU) 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, includes prophylactic treatment or treatment that prevents one or more symptoms or conditions of a disease, disorder, or conditions described herein (e.g., activated fibroblast associated disease or pre-disease state), or may refer to a treatment of a pre-disease state. Treatment can be initiated, for example, prior to ("pre-exposure prophylaxis") or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, includes compounds which are rapidly transformed in vivo to the parent compound of the above formula. Prodrugs also encompass bioequivalent compounds that, when administered to a human, lead to the in vivo formation of an intracellular $Ca^{2+}$ elevator, including cardiac glycosides, a YAP/TAZ inhibitor, and/or a chemical listed in Tables 1 and 2, or any pharmacologically acceptable salt, solvate, ester, amide, clathrate, stereoisomer, enantiomer, prodrug, or analog thereof, or a combination thereof.

As used herein, and as well understood in the art, "treatment" includes an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also refer to delaying the onset of, impeding or reversing the progress of, or alleviating either the disease or condition to which the term applies, or one or more symptoms of such disease or condition.

The term "unit dosage forms" includes physically discrete units suitable as unitary dosages for human subjects and other mammals, each unit containing a predetermined quantity of active material calculated to produce the desired therapeutic effect, in association with any suitable pharmaceutical excipient or excipients.

The present compounds can be prepared from readily available starting materials using the methods and procedures known in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one of ordinary skill in the art by routine optimization procedures.

Pharmaceutical Compositions: The methods described herein can also include the administrations of pharmaceutically acceptable compositions that include intracellular $Ca^{2+}$ elevators, including cardiac glycosides, YAP/TAZ inhibitors, and/or chemicals listed in Tables 1 and 2, or any pharmacologically acceptable salt, solvate, ester, amide, clathrate, stereoisomer, enantiomer, prodrug, or analog thereof, or a combination thereof. Pharmaceutical compositions and dosage forms of the invention comprise one or more active ingredients in relative amounts and formulated so that a given pharmaceutical composition or dosage form inhibits activated fibroblast associated disease or pre-disease state cell proliferation or other disease or condition where inhibiting the hepatocyte growth factor receptor can therapeutically influence the respective disease or condition progression. Preferred pharmaceutical compositions and dosage forms comprise an intracellular $Ca^{2+}$ elevator, including cardiac glycosides, a YAP/TAZ inhibitor, and/or a chemical listed in Tables 1 and 2, or any pharmacologically acceptable salt, solvate, ester, amide, clathrate, stereoisomer, enantiomer, prodrug, or analog thereof, or a combination thereof, optionally in combination with one or more additional active agents. When employed as pharmaceuticals, any of the present active agents can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention (e.g., an intracellular $Ca^{2+}$ elevator, including cardiac glycosides, a YAP/TAZ inhibitor, and/or a chemical listed in Tables 1 and 2, or any pharmacologically acceptable salt, solvate, ester, amide, clathrate, stereoisomer, enantiomer, prodrug, or analog thereof, or a combination thereof) can be administered alone, combined, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are described in *Remington: The Science and Practice of Pharmacy,* $21^{st}$ Ed., Gennaro, Ed., Lippencott Williams & Wilkins (2005), a well-known reference text in this field, and in the USP/NF (United States Pharmacopeia and the National Formulary). In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. Other exemplary excipients are described in *Handbook of Pharmaceutical Excipients,* $6^{th}$ Edition, Rowe et al., Eds., Pharmaceutical Press (2009).

The pharmaceutical compositions can be formulated so as to provide immediate, extended, or delayed release of the active ingredient after administration to the patient by employing procedures known in the art.

In addition to other dosages listed herein, the pharmaceutical compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or from about 100 mg to about 250 mg of the active ingredient. For preparing solid compositions such as tablets, the active agent may be mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration. The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active agent by controlling the dissolution and/or the diffusion of the active agent substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the administered therapeutic or drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, rnethyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions suitable for oral mucosal administration (e.g., buccal or sublingual administration) include tablets, lozenges, and pastilles, where the active ingredient is formulated with a carrier, such as sugar, acacia, tragacanth, or gelatin and glycerine.

Coatings: The pharmaceutical compositions formulated for oral delivery, such as tablets or capsules of the present invention can be coated or otherwise compounded to provide a dosage form affording the advantage of delayed or extended release. The coating may be adapted to release the active agent in a predetermined pattern (e.g., in order to achieve a controlled release formulation) or it may be adapted not to release the active agent until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropyicellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the active agent is released in the lower gastrointestinal tract.

In addition to coatings that effect delayed or extended release, the solid tablet compositions may include a coating adapted to protect the composition from unwanted chemical changes (e.g., chemical degradation prior to the release of the active agent). The coating may be applied on the solid dosage form in a similar manner as that described in *Encyclopedia of Pharmaceutical Technology*, vols. 5 and 6, Eds. Swarbrick and Boyland, 2000.

Parenteral Administration: Within the scope of the present invention are also parenteral depot systems from biodegradable polymers. These systems are injected or implanted into the muscle or subcutaneous tissue and release the incorporated active agent over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 µm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Mucosal Drug Delivery: Mucosal drug delivery (e.g., drug delivery via the mucosal linings of the nasal, rectal, vaginal, ocular, or oral cavities) can also be used in the methods described herein. Methods for oral mucosal drug delivery include sublingual administration (via mucosal membranes lining the floor of the mouth), buccal administration (via mucosal membranes lining the cheeks), and local delivery (Harris et al., *Journal of Pharmaceutical Sciences*, 81(1): 1-10, 1992)

Oral transmucosal absorption is generally rapid because of the rich vascular supply to the mucosa and allows for a rapid rise in blood concentrations of the therapeutic or active agent ("American Academy of Pediatrics: Alternative Routes of Drug Administration—Advantages and Disadvantages (Subject Review)," *Pediatrics*, 100(1):143-152, 1997).

For buccal administration, the compositions may take the form of, e.g., tablets, lozenges, etc. formulated in a conventional manner. Permeation enhancers can also be used in buccal drug delivery. Exemplary enhancers include 23-lauryl ether, aprotinin, azone, benzalkonium chloride, cetylpyridinium chloride, cetyltrimethylammonium bromide, cyclodextrin, dextran sulfate, lauric acid, lysophosphatidylcholine, methol, methoxysalicylate, methyloleate, oleic acid, phosphatidylcholine, polyoxyethylene, polysorbate 80, sodium EDTA, sodium glycholate, sodium glycodeoxycholate, sodium lauryl sulfate, sodium salicylate, sodium taurocholate, sodium taurodeoxycholate, sulfoxides, and alkyl glycosides. Bioadhesive polymers have extensively been employed in buccal drug delivery systems and include cyanoacrylate, polyacrylic acid, hydroxypropyl methylcellulose, and poly methacrylate polymers, as well as hyaluronic acid and chitosan.

Liquid drug formulations (e.g., suitable for use with nebulizers and liquid spray devices and electrohydrodynamic (EHD) aerosol devices) can also be used. Other methods of formulating liquid drug solutions or suspension suitable for use in aerosol devices are known to those of skill in the art.

Formulations for sublingual administration can also be used, including powders and aerosol formulations. Exemplary formulations include rapidly disintegrating tablets and liquid-filled soft gelatin capsules.

Dosing Regimens: The present methods for treating activated fibroblast associated disease or pre-disease state are carried out by administering one or more intracellular $Ca^{2+}$ elevators, including cardiac glycosides, YAP/TAZ inhibitors, and/or chemicals listed in Tables 1 and 2, or any pharmacologically acceptable salt, solvate, ester, amide, clathrate, stereoisomer, enantiomer, prodrug, or analog thereof, or a combination thereof for a time and in an amount sufficient to result in stabilization and/or reversal of activated fibroblast associated disease or pre-disease state symptoms, or other disease or condition where inhibiting the hepatocyte growth factor receptor can therapeutically influence the respective disease or condition progression. The amount and frequency of administration of the compositions can vary depending on, for example, what is being administered, the state of the patient, and the manner of administration. The dosage is likely to depend on such variables as the type and extent of progression of the activated fibroblast associated disease or pre-disease state, the severity of the activated fibroblast associated disease or pre-disease state, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of activated fibroblast associated disease or pre-disease state or slowing its progression.

The amount of active agent per dose can vary. For example, a subject can receive from about 0.1 µg/kg to about 50,000 µg/kg. Generally, the active agent is administered in an amount such that the peak plasma concentration ranges from 1.50 nM-250 µM.

Exemplary dosage amounts can fall between 0.1-5000 µg/kg, 100-1500 µg/kg, 100-350 µg/kg, 340-750 µg/kg, or 750-1000 µg/kg. Exemplary dosages can 0.25, 0.5, 0.75, 1.0, or 2.0 mg/kg. In another embodiment, the administered dosage can range from 0.05-5 mmol of an active agent (e.g., 0.089-3.9 mmol) or 0.1-50 µmol of an active agent (e.g., 0.1-25 µmol or 0.4-20 µmol).

The frequency of treatment may also vary. The subject can be treated one or more times per day with the active agent (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

KITS: Any of the pharmaceutical compositions of the invention described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention to reduce incidence, duration, and or severity of activated fibroblast associated disease or pre-disease state.

The disclosed invention relates to products and methods of treating an activated fibroblast associated disease or pre-disease condition in a mammal comprising administering a pharmaceutical composition including a therapeutically effective amount of a first therapeutic; wherein the first therapeutic is one of an intracellular $Ca^{2+}$ elevator, a YAP/TAZ inhibitor, both a intracellular $Ca^{2+}$ elevator and a YAP/TAZ inhibitor, or pharmacologically acceptable salts, solvates, esters, amides, clathrates, stereoisomers, enantiomers, prodrugs or analogs thereof, or a combination thereof. According to a further embodiment the first therapeutic includes an intracellular $Ca^{2+}$ elevator or a pharmacologically acceptable salt, solvate, ester, amide, clathrate, stereoisomer, enantiomer, prodrug or analog thereof, or a combination thereof. According to a further embodiment the intracellular $Ca^{2+}$ elevator inhibits sodium-potassium ATPase. According to a further embodiment the intracellular $Ca^{2+}$ elevator is a cardiaoglycoside. According to a further embodiment the intracellular $Ca^{2+}$ elevator is selected from a group comprising menthol, linalool (3,7-dimethylocta-1, 6-dien-3-ol), geraniol ((trans)-3,7-Dimethyl-2,6-octadien-1-ol), hydroxy-citronellal (7-hydroxy-3,7-dimethyloctanal), WS-3 (N-ethyl-5-methyl-2-propan-2-ylcyclohexane-1-carboxamide), WS-23 (N,2,3-trimethyl-2-propan-2-ylbutanamide), Frescolat MGA ((9-methyl-6-propan-2-yl-1,4-dioxaspiro[4.5]decan-2-yl)methanol), Frescolat ML ([(1R,2S, 5R)-5-methyl-2-propan-2-ylcyclohexyl] 2-hydroxypropanoate), PMD 38 (2-(1-Hydroxy-1-methylethyl)-5-methylcyclohexanol), Coolact P ((1R,2R,5S)-5-methyl-2-prop-1-en-2-ylcyclohexan-1-ol), Cooling Agent 10 (3-(I-Menthoxy)propane-1,2-diol), and rotundifolone ((1S,6S)-6-methyl-3-propan-2-ylidene-7-oxabicyclo[4.1.0] heptan-2-one). According to a further embodiment the first therapeutic includes a YAP/TAZ inhibitor or a pharmacologically acceptable salt, solvate, ester, amide, clathrate, stereoisomer, enantiomer, prodrug or analog thereof, or a combination thereof. According to a further embodiment the YAP/TAZ inhibitor is one of αE-catenin, thiazovivin, cucurbitacin I, dasatinib, fluvastatin, pazopanib, a statin, and pyrvinium. According to a further embodiment the YAP/TAZ inhibitor is pyrvinium prepared with a variable counter anion including one of a halide, tosylate, triflate and pamoate. According to a further embodiment the pharmaceutical composition further includes a therapeutically effective amount of a second therapeutic, wherein the second therapeutic is chemically distinct from the first therapeutic. According to a further embodiment the second therapeutic is one of an intracellular $Ca^{2+}$ elevator, a YAP/TAZ inhibitor, both a intracellular $Ca^{2+}$ elevator and a YAP/TAZ inhibitor, or pharmacologically acceptable salts, solvates, esters, amides, clathrates, stereoisomers, enantiomers, prodrugs or analogs thereof, or a combination thereof. According to a further embodiment the second therapeutic is one of gemcitabine, Nab-paclitaxel, and both gemcitabine and Nab-paclitaxel. According to a further embodiment the second therapeutic is one of nintedanib, pincenidone, and both nintedanib and pirfenidone. According to a further embodiment the second therapeutic is one of a cardioglycoside, an intracellular $Ca^{2+}$ elevator, a sodium-potassium ATPase inhibitor, an anti-cancer chemical, a protein synthesis inhibitor, an antimicrobial, an anti-parasitic, YAP/TAZ inhibitor, a macrolide antibiotic, an anthracycline antibiotic, a topoisornerease inhibitor, a diterpenoid epoxide, a tryptamin, and an antiarythmic. According to a further embodiment the activated fibroblast associated disease or pre-disease condition is one of fibrosis, pulmonary fibrosis, Cystic fibrosis, idiopathic pulmonary fibrosis, radiation-induced lung injury, non-alcoholic fatty liver disease, non-alcoholic steatohepatitis, cirrhosis, hepatocellular carcinoma, cardiac fibrosis, atrial fibrosis, endomycocardial fibrosis, old myocardial fibriosis, glial scarring (gliosis), renal fibrosis, pancreatic cancer, arthrofibrosis, crohn's disease, dupuytren's contracture, myofibroblastic tumors, mediastinal fibrosis, retroperitoneal cavity fibrosis, myelofibrosis, keloid/skin fibrosis, pyronie's disease, nephrogenic systemic fibrosis, progressive massive fibrosis, retroperitoneal fibrosis, scleroderma/systemic sclerosis, adhesive capsulitis and cancers with solid tumors, or respective pre-disease conditions thereof. According to a further embodiment the activated fibroblast associated disease or pre-disease condition is a type of cancer. According to a further embodiment the activated fibroblast associated disease or pre-disease condition is a non-cancer disease. According to a further embodiment the mammal is a human. According to a further embodiment the first therapeutic is administered in a microMolar concentration.

The disclosed invention further relates to products and methods of treating an activated fibroblast associated disease or pre-disease condition in a mammal comprising administering a pharmaceutical composition including a therapeutically effective amount of a first therapeutic, wherein the first therapeutic is one of a cardioglycoside, an intracellular $Ca^{2+}$ elevator, a sodium-potassium ATPase inhibitor, an anti-cancer chemical, a protein synthesis inhibitor, an antimicrobial, an anti-parasitic, YAP/TAZ inhibitor, a macrolide antibiotic, an anthracycline antibiotic, a topoisomerease inhibitor, a diterpenoid epoxide, a tryptamin, and an antiarythmic. According to a further embodiment the pharmaceutical composition further includes a therapeutically effective amount of a second therapeutic, the second therapeutic is one of a cardioglycoside, an intracellular $Ca^{2+}$ elevator, a sodium-potassium ATPase inhibitor, an anti-cancer chemical, a protein synthesis inhibitor, an antimicrobial, an anti-parasitic, YAP/TAZ inhibitor, a macrolide antibiotic, an anthracycline antibiotic, a topoisomerease inhibitor, a diterpenoid epoxide, a tryptamin, and an antiarythmic, and the first therapeutic and the second therapeutic are therapeutic through functioning via different biochemical pathways. According to a further embodiment, one of the first therapeutic and the second therapeutic are one of digitoxigenin, digoxin, strophantine octahydrate, lanatoside C, helveticoside, strophanthidin, digoxigenin, proscillaridin a, doxorubicin hydrochloride, daunorubicin hydrochloride, camptothecine, azacytidine-5, lycorine hydrochloride, cycloheximide, methyl benzethonium chloride, ivermectin, emetine dihydrochloride, pyrvinium pamoate, oleandomycin phosphate, topotecan, irinotecan, etoposide, idaruicin, doxorubicin, epiruicin, triptolide, nonyloxytrytamin, and amdiodarone, or pharmacologically acceptable salts, solvates, esters, amides, clathrates, stereoisomers, enantiomers, prodrugs or analogs thereof, or a combination thereof.

The disclosed invention also relates to therapeutic methods and products comprising a first pharmaceutically active agent being one of a one of an intracellular $Ca^{2+}$ elevator, a YAP/TAZ inhibitor, both a intracellular $Ca^{2+}$ elevator and a YAP/TAZ inhibitor, or pharmacologically acceptable salts, solvates, esters, amides, clathrates, stereoisomers, enantiomers, prodrugs or analogs thereof, or a combination thereof, and a second pharmaceutically active agent being one of an one of intracellular $Ca^{2+}$ elevator, a YAP/TAZ inhibitor, both a intracellular $Ca^{2+}$ elevator and a YAP/TAZ inhibitor, or pharmacologically acceptable salts, solvates, esters, amides, clathrates, stereoisomers, enantiomers, prodrugs or analogs thereof, or a combination thereof, wherein the first pharmaceutically active agent is chemically distinct from the second pharmaceutically active agent.

This invention also relates to pharmaceuticals that can be used therapeutically to prevent or reverse an activated fibroblast phenotype and pathologies that are a result of and/or exacerbated by hyperactive fibroblasts; and laboratory method for screening and identifying such drugs.

This invention also relates to the screen methodology used to discover the therapeutic drugs disclosed, including the method of identifying drugs to prevent induction of the activated fibroblast phenotype and utilizing automated immunofluorescence imagining and quantification.

Activated fibroblast phenotype include fibroblasts that exhibit increased proliferation or defective apoptosis, and/or enhanced contractility, elevated expression of extracellular matrix components including, but not limited to, fibronectin, Type I, III, IV, and V collagen, tenascin C, Periostin, laminins, proteoglycans, and glycoproteins, and/or elevated expression of myofibroblast protein markers including smooth muscle actin, vimentin, TAZ, PDGFRβ and FAP; and/or reduced expression of FSP1; elevated secretion VEGFA, HGF, EGF, IGF, PDGF, TNF, IFNγ, SDF1, IL-6, IL-8, $PGE_2$, CTGF, CXCL7, MMPs, IL-4, IL-10, TGFβ, CCL2, CCL5, CXCL9, CXCL10, nitric oxide; and/or driven by cell signaling pathways activated by Wnt ligands, TGF-β, FGF, IL-8, PDGF, and/or IL-6.

Activated fibroblast may include at least the distinct fibroblast cell types of fibrocytes, myofibroblasts, hepatic stellate cells, pancreatic stellate cells, chollagenoblast, desmocyte.

Associated with pathologies including but not limited to: fibrosis, pulmonary fibrosis, Cystic fibrosis, idiopathic pulmonary fibrosis, radiation-induced lung injury, non-alcoholic fatty liver disease, nonalcoholic steatohepatitis, cirrhosis, hepatocellular carcinoma, cardiac fibrosis, atrial fibrosis, endomycocardial fibrosis, old myocardial fibriosis, glial scarring (gliosis), renal fibrosis, pancreatic cancer, arthrofibrosis, crohn's disease, dupuytren's contracture, myofibroblastic tumors, mediastinal fibrosis, retroperitoneal cavity fibrosis, myelofibrosis, keloid/skin fibrosis, pyronie's disease, nephrogenic systemic fibrosis, progressive massive fibrosis, retroperitoneal fibrosis, scleroderma/systemic sclerosis, adhesive capsulitis and cancers with solid tumors.

Based on the disclosed data, additional cardioglycosides to those listed in Table 1, that are arguably therapeutic include Ouabain/Strophanthin, Deslanoside, and Lanatoside A.

Based on the disclosed data, additional therapeutic chemicals are believed to be those that activate CAMKII, and/or prevent translocation of SMAD.

Based on the disclosed data, additional therapeutic chemicals are believed to be those that activate casein kinase 1 and/or promotes degradation of TAZ.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that though the accompanying drawings are not substantially to scale, the emphasis is instead placed on illustrating the principles of the invention. The invention will now be described, by way of example, with reference to the accompanying drawings in which:

FIGS. 2A-2E: Parameters for a High Content Imaging Screen to Identify Inhibitors of CAF Differentiation. A. WPMY-1 cells were plated into each well of 4-chamber slice (for IF), or (C) in a 24 well plate (for western blot analysis). After cell attachment, vehicle or 5 ng/ml TGF-β was added into each well and incubated for 24 h in a 37° C. in a humidified incubator containing 5% $CO_2$. For fluorescence detection (A), cells were fixed and stained with antibody detecting fibronectin and/or stained with DAPI to detect the nuclei. Protein was extracted with boiling Lamaelli buffer for WB (C) and blots were probed with anti-fibronectin or anti-tubulin antibodies. Fibronectin fluorescence (D and E) was measured in the presence or absence of TGF-β in 8 well replicates as follows. Cells were conditioned in serum-free DMEM for 48 hr prior to the addition of TGF-β. Images were acquired using a Cellomics platform with a mask shown in the schematic of (B). The mean of the total fluorescence intensity in each well was calculated from 300 cells per image field and up to 15 fields from each well for fibronectin. The fold change in fibronectin expression per acquired image (nuclei) is shown (Mean+/−SD). Excellent reproducibility between runs was observed with a Z score of 0.6 and a signal to noise of three.

FIGS. 4A-4H: Dose response for identified hits. As shown in the four panels of FIG. 4A, fibronectin fluorescence was measured from images acquired following a Cellomics scan using WPMY-1 cells with concentrations of hits over a range of 0-100 uM. TGF-β was added along with the indicated testing compound for 24-hour except for vehicle control where only medium was added. Results were expressed as percent inhibition caused by cells treated with TGF-β alone and without testing compound, which was considered as 100%. Data represents Mean±STD of 4 replicated wells. Panel B is a western blot analysis demonstrating that fibronectin levels detected using this method are consistent with the observations quantitated by the Cellomics system. Graphs of concentration of a given "hit" chemical (in μM, antilog) to inhibition (TGF-β as 100%) are shown panels C—H of Strophatine (4C), Digoxin (4D), Digitoxigenin (4E), Ivermectin (4F), Pyruvinium (4G), and Emetine (4H) respectively.

Figures 9A, 9B:
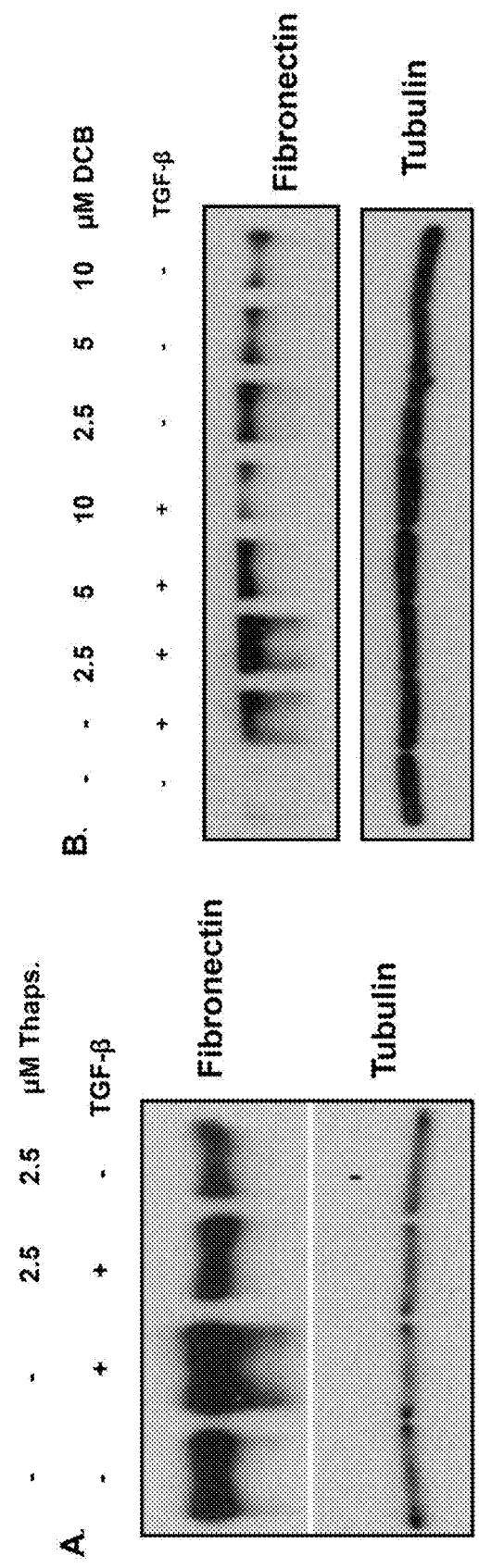

FIGS. 9A-9B: Increases in intracellular $Ca^{2+}$ prevent TGF-β-induced fibronectin expression. (A) WPMY-1 fibroblasts were treated with 2.5 µM thapsigargin±5 ng/ml TGF-β for 24 hours. (B) WPMY-1 fibroblasts were treated with 2.5-10 µM 3',4'-dichlorobenzamil hydrochloride (DCB)±5 ng/ml TGF-β for 24 hours. Cell lysates were analyzed by western blot for fibronectin expression.

Figure 10C:
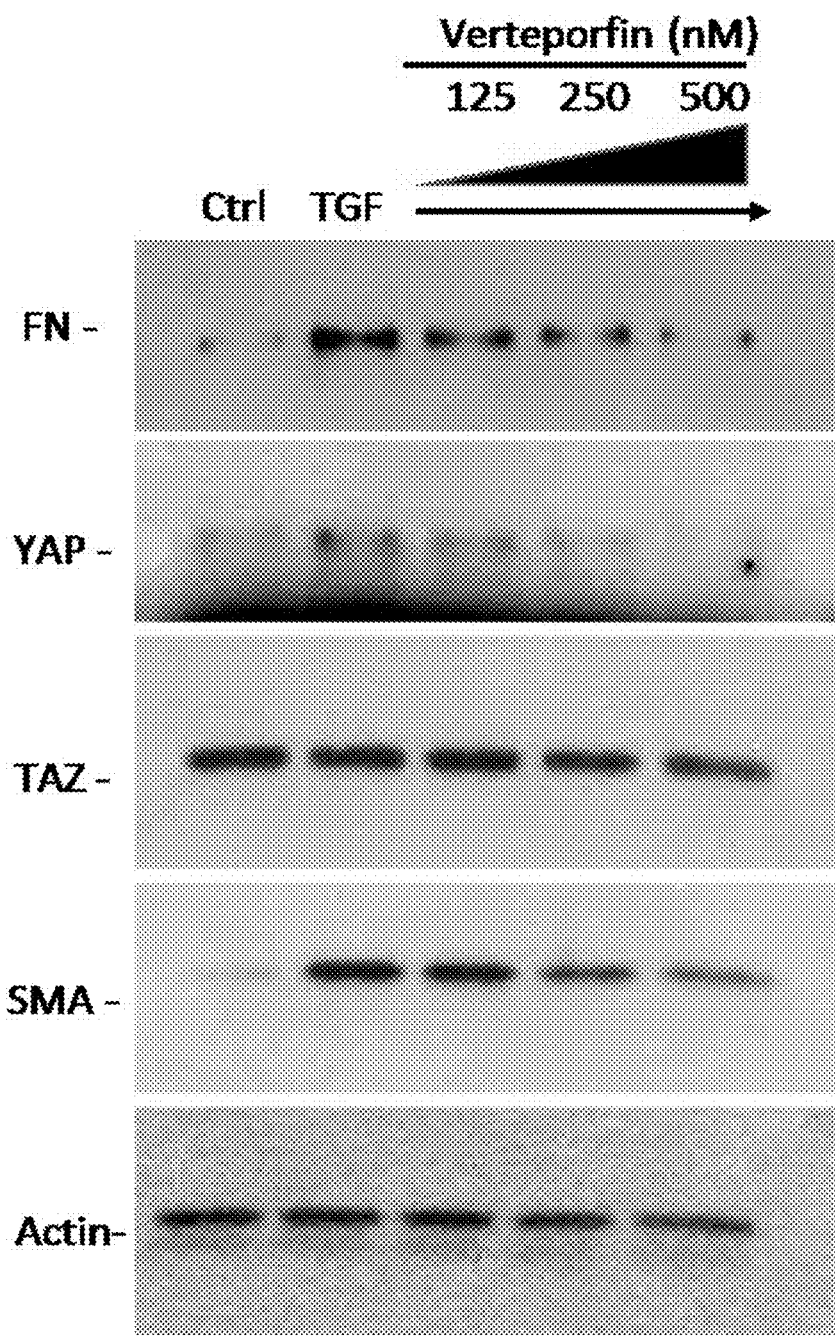
Figures 11A, 11B, 11C, 11D, 11E, 11F:
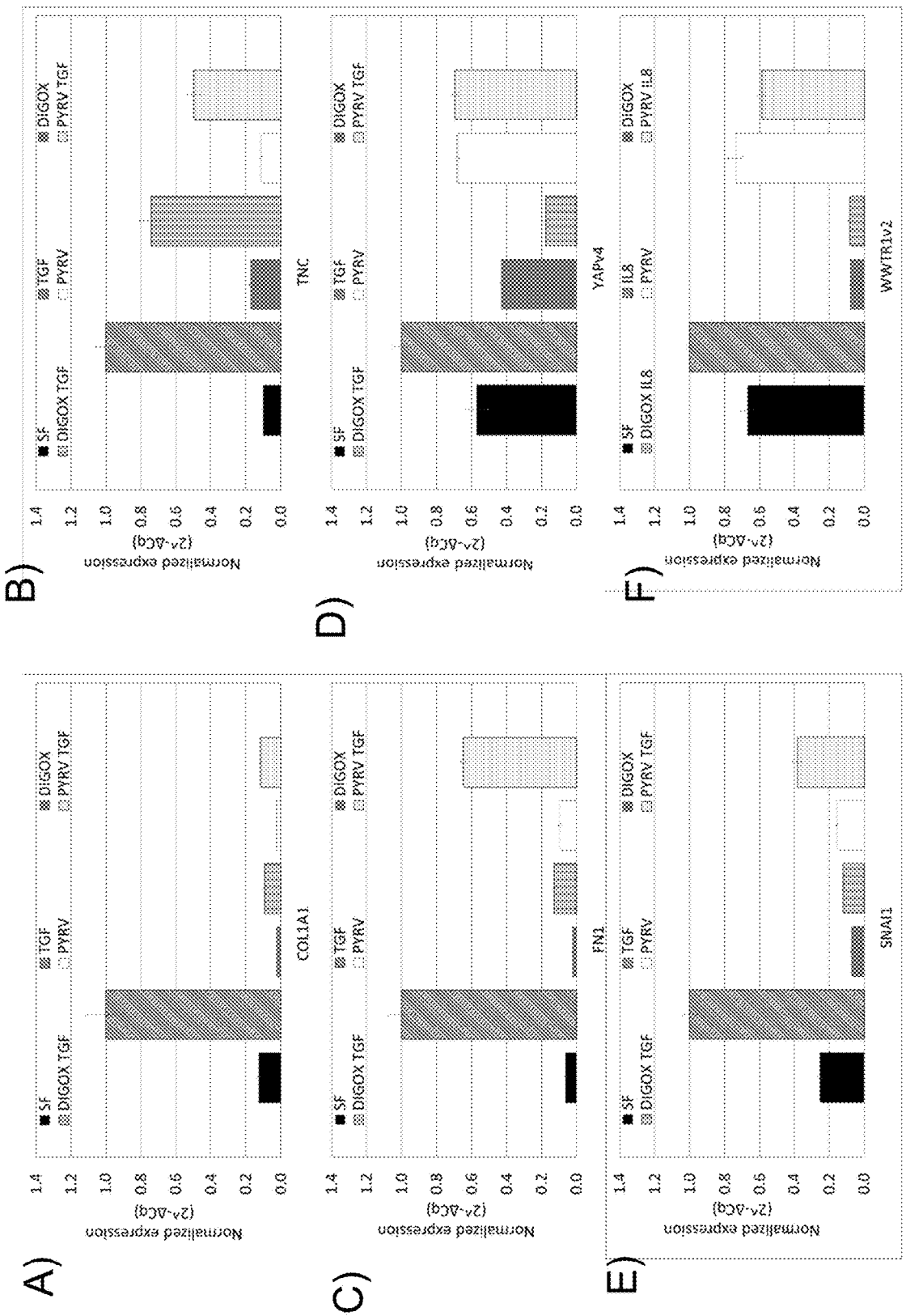

FIGS. 10A-10C: Digoxin and pyrvinium individually block the induction of activated fibroblasts by TGF-β or TGF-β with FGF in a dose dependent manner. FIG. 10A: MRC-5 lung fibroblast cells were serum-starved 24 hours then treated with 10 ng/mL TGF-β in serum-free media for 24 hours with or without pyrvinium or digoxin at the indicated concentration. FIG. 10B: MRC-5 lung fibroblast cells were serum-starved 24 hours then treated with 10 ng/mL TGF-β and 20 ng/ml FGF in serum-free media for 24 hours with or without pyrvinium or digoxin at the indicated concentration. FIG. 10C: MRC-5 lung fibroblast cells were serum-starved 24 hours then treated with 10 ng/mL TGF-β in serum-free media for 24 hours with or without verteporfin at the indicated concentration. FN: fibronectin, YAP: yes-activated protein, TAZ: transcriptional coactivator with PDZ-binding motif, and SMA(ACTA2): smooth muscle actin. Representative western blot is shown (n=3).

FIGS. 11A-11F: Digoxin and pyrvinium can each prevent the transcriptional upregulation of activated fibroblasts markers by TGF-β or IL-8. MRC-5 cells were serum-starved for 24 hours then spiked with or without 10 ng/mL TGF-β or 20 ng/ml IL-8 as indicated for 24 hours with or without digoxin (150 nM) or pyrvinium (300 nM). Expression of the indicated genes was analyzed by real-time qPCR. TGFβ treated samples were set at 1 and other conditions were normalized accordingly. FN1: fibronectin, YAPv4: yes-activated protein, TNC: tenascin C, Col1A1: collagen 1a1, WWTR1v2: WW domain-containing transcription regulator protein 1 (TAZ), and SNAI1: Snail1. Representative data from at least two independent experiments are provided.

Figures 12A, 12B:
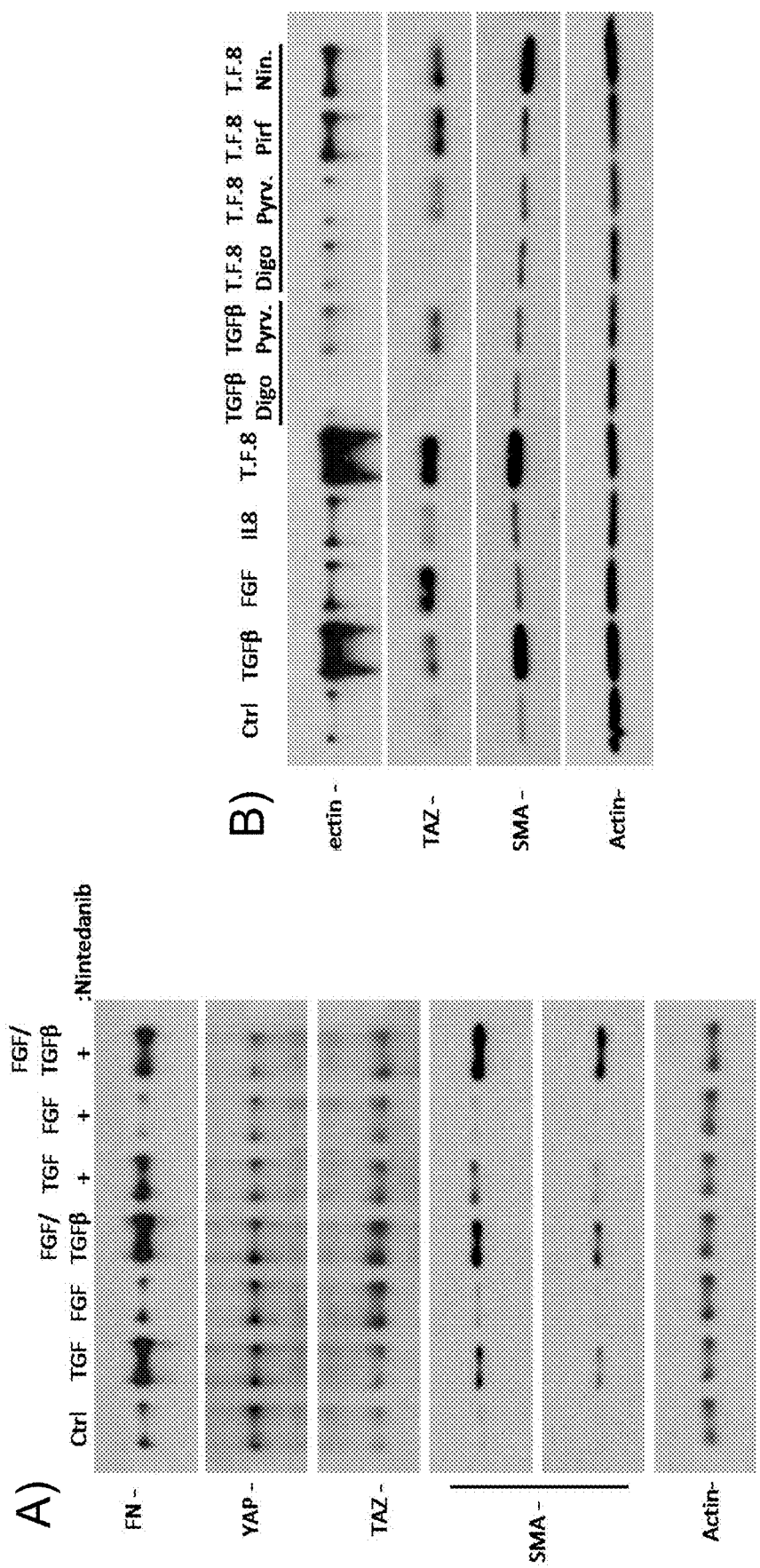
Figures 12C, 12D:
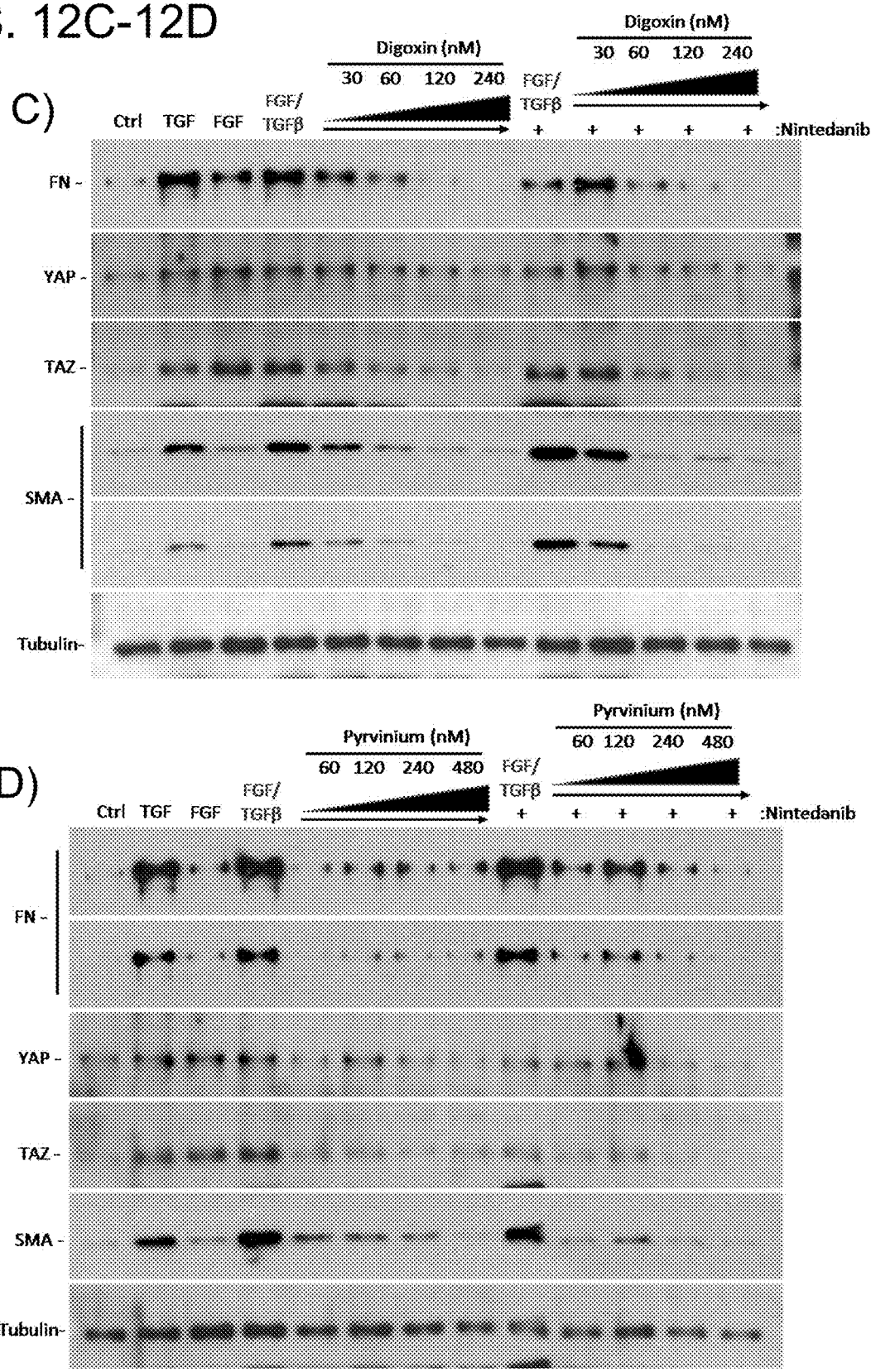

FIGS. 12A-12D: Digoxin and pyrvinium are effective at repressing fibroblast induction by multiple growth factors more completely than the standard anti-fibrotic agents nintedanib (a tyrosine kinase inhibitor) or pirfenidone. FIG. 12A: MRC-5 cells were serum-starved 24 hours then treated with 10 ng/mL TGF-β and/or 10 ng/mL FGF in serum-free media for 24 hours with or without nintedanib (200 nM). FIG. 12B: MRC-5 lung fibroblast cells were serum-starved for 24 hours then treated with 10 ng/mL TGF-β, 20 ng/mL FGF, and/or 20 ng/mL IL-8 in serum-free media 24 hours in the presence or absence of digoxin (250 nM), pyrvinium (500 nM), pirfenidone (500 µm), or nintedanib (250 nM). T.F.8: combination TGF, FGF, IL8. Together these demonstrate the efficacy of nintedanib is limited to FGF, whereas digoxin and pyrvinium are effective against TGF-β and FGF signaling. FIGS. 12C-12D: MRC-5 lung fibroblast cells were serum-starved 24 hours then treated with 10 ng/mL TGF-β and 20 ng/ml FGF in serum-free media for 24 hours with or without (FIG. 12C) digoxin or (FIG. 12D) pyrvinium at the indicated concentration with or without nintedanib (200 nM). FN: fibronectin, YAP: yes-activated protein, TAZ: transcriptional coactivator with PDZ-binding motif, and SMA(ACTA2): smooth muscle actin. Representative western blot is shown (n=2).

Figure 13A:
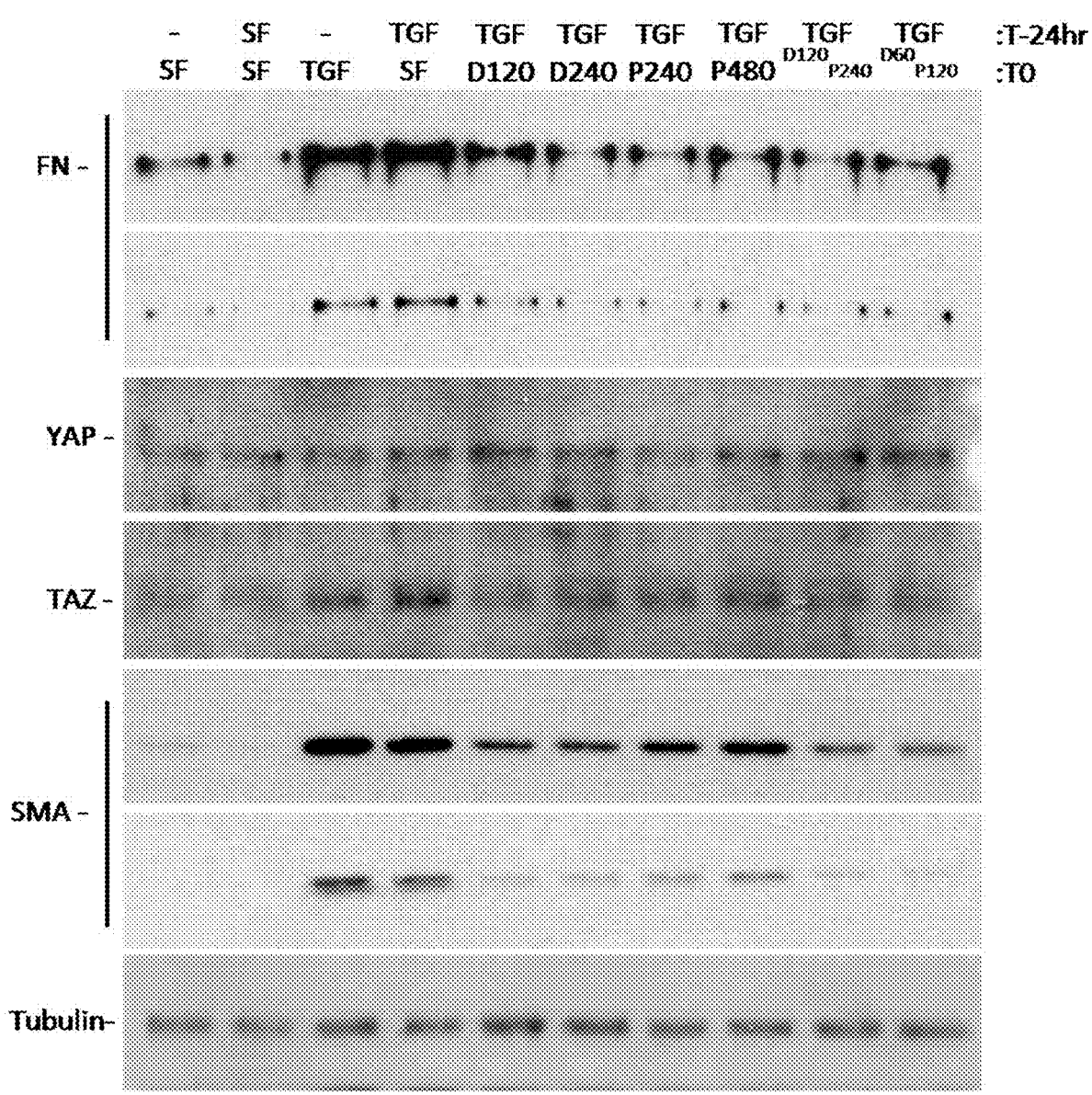
Figure 13B:
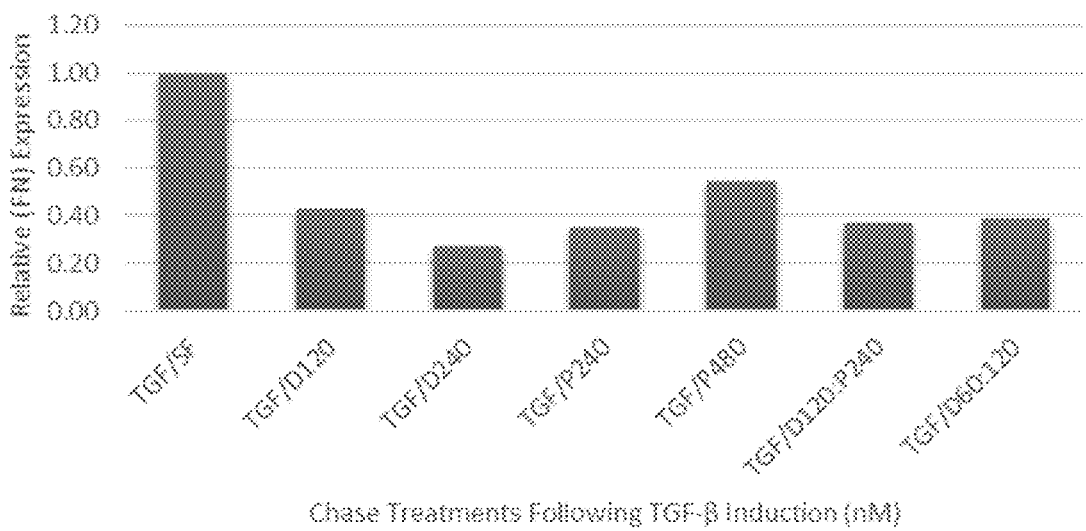
Figure 13C:
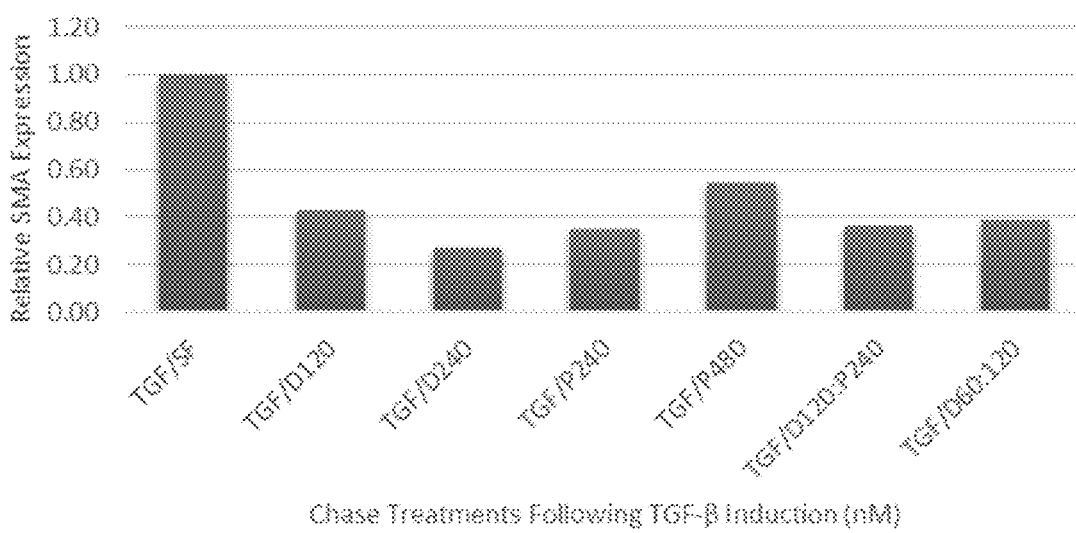
Figures 13D, 13E:
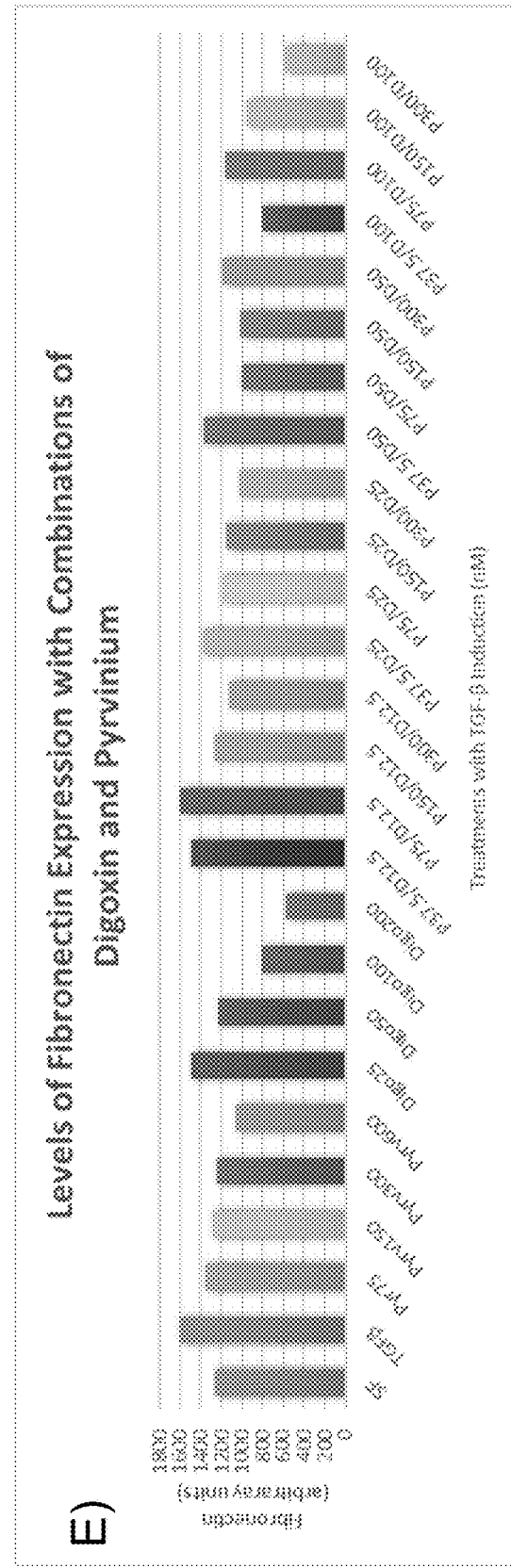

FIGS. 13A-13E: Digoxin and pyrvinium can reverse an activated fibroblast phenotype and can act additively in combination to inhibit the activated fibroblast phenotype. FIGS. 13A-13C: MRC-5 lung fibroblast cells were serum-starved 24 hours then treated with or without 10 ng/mL TGF-β for 24 hours (T-24 hr). For an additional 24 hours (T0), cells were washed or not, and treated with or without pyrvinium or digoxin at the indicated concentration alone or in combination in serum-free media to demonstrate reversing of the activated phenotype. FN: fibronectin, YAP: yes-activated protein, TAZ: transcriptional coactivator with PDZ-binding motif, and SMA(ACTA2): smooth muscle actin. Representative western blot is shown (n=2). FIGS. 13D-13E: MRC-5 cells were serum-starved 24 hours then treated with 10 ng/mL TGF-β in serum-free media for 24 hours with or without pyrvinium (pyr[nM]) or digoxin (digo[nM]) at the indicated concentrations. Cells were fixed in −20C methanol for 15 minutes and immunolabeled for fibronectin. Cellomics arrayscan imaging was performed and staining intensity was quantified and analyzed for fibronectin expression on a per cell basis. Values are displayed as a graph as well as arrayed for better visualization of combination effects. (n=2)

FIGS. 14-15 show Table I—Prestwick Library and Table II—NIH Library chemicals respectively. These tables show chemicals that produced a hit. A "hit" was defined as a compound causing at least 50% reduction of "Mean_Ring-Total Intensity", which is the fluorescence intensity within the defined ring (see FIG. 2) surrounding nucleus of each cell, summed for 300 cells per image and 15 fields per image. The solvent, 0.1% Dimethyl Sulfoxide (DMSO), with and without TGF-beta served as an internal control on each plate to normalize day-to-day and plate-to-plate variation with DMSO alone as low fluorescence (0%) and TGF-β treated as maximal fluorescence (100%). Normalization (percent inhibition) was computed as: $(F_{TGF\beta}$ minus $F_{compound})/(F_{TGF\beta}$ minus $F_{DMSO})$ with $F_{compound}$=fluorescence reading for TGF-β+ compound treated cells, $F_{TGF\beta}$=fluorescence reading for TGF-beta alone treated control, and $F_{DMSO}$=fluorescence reading for 0.1% DMSO treated control.

DETAILED DESCRIPTION OF THE PREFERRED EMBODIMENTS

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the content excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Figures 1A, 1B, 1C, 1D:
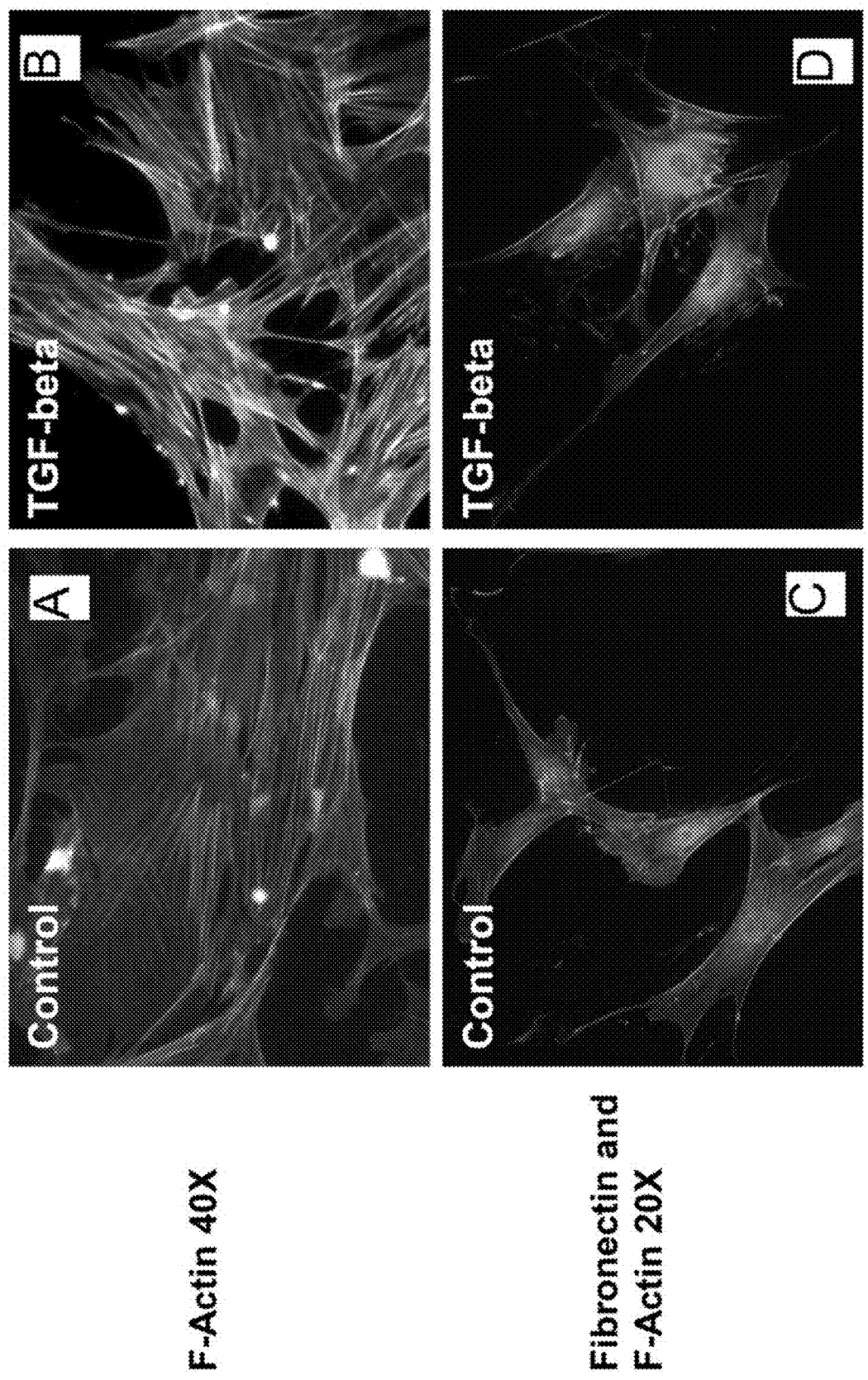
FIGS. 1A-1D: Immunofluorescence microscopy experiment visualized in 4 panels to detect fibronectin. The data demonstrate the robust induction of fibronectin by TGF-β over a 24 hour time period.
Figure 2A:
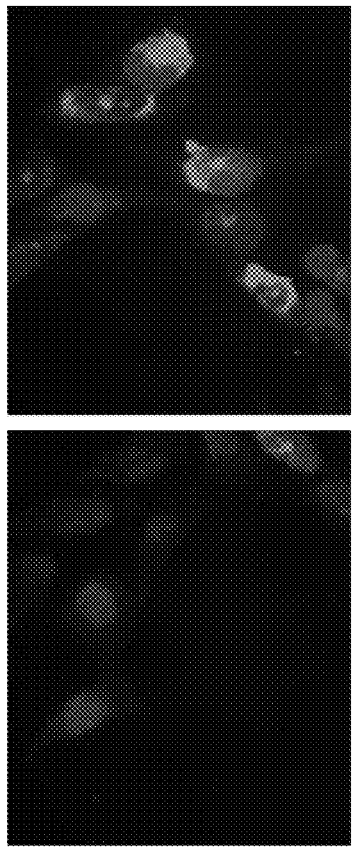
Figure 2B:
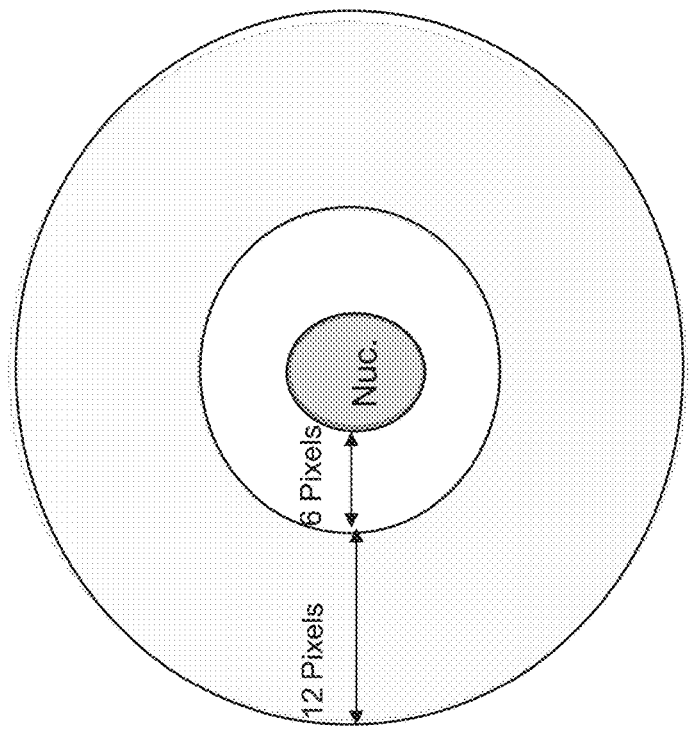
Figure 2C:
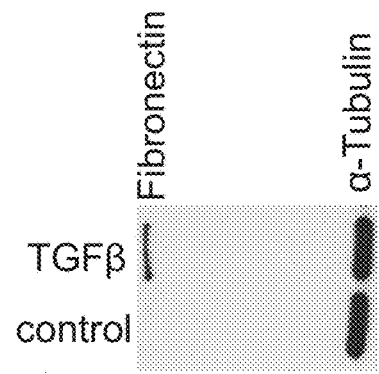
Figure 2D:
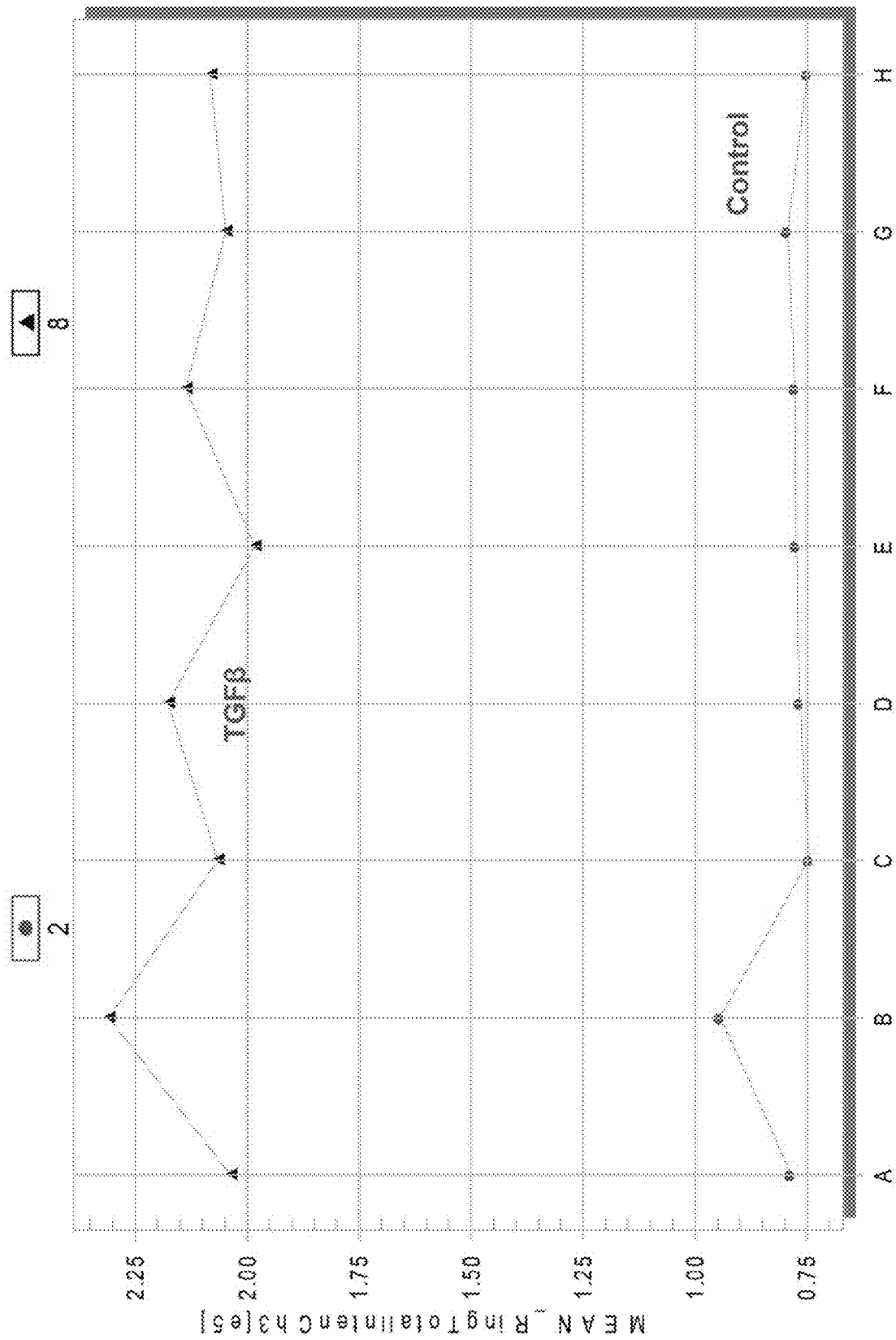

Turning now to FIG. 1, a brief description concerning the various components of the present invention will now be briefly discussed. The WPMY-1 fibroblast cell line was derived from the peripheral zone of a histologically normal prostate and expresses low basal levels of activated myofibroblast markers, including fibronectin and alpha smooth muscle actin (α-SMA). FIGS. 1A and 1B demonstrate, by Western blot analysis and immunofluorescence microscopy, that TGF-β robustly induces fibronectin following an overnight incubation. The high expression of fibronectin by activated fibroblasts, as well as its overexpression in cancer and fibrotic diseases makes it an excellent target for drug discovery. Using TGF-β as an inducer of the fibronectin and the CAF phenotype, the inventors developed a high-content immunofluorescence (I.F.)-based screen to identify repurposed drugs capable of blocking the induction of fibronectin.

Protocol for High Content Screening for Inhibitors of Fibronectin Induction by TGF-beta. The 1280 compound Prestwick Chemical Library (Prestwick Chemical, Illkirch-Graffenstaden, France) and the NIH clinical collection (451 compounds) consists of FDA approved compounds (Prestwick) and compounds that have a history of use in clinical trials (NIH collection). All compounds were provided by the manufacturer at a concentration of 10 mM in DMSO. Cells were seeded at $7 \times 10^3$ cells per well in a 96-well plate. The following day, media was changed to serum-free DMEM for 24 hours. After serum-starvation, cells were treated with 5 ng/mL TGF-β and 10 μM (final DMSO concentration of <0.1%) of each screening compound for 24 hours. The solvent, 0.1% DMSO±TGF-β (negative and positive control) in 8 wells each served as an internal control on each plate to normalize day-to-day and plate-to-plate variation. Cells were then fixed with 100% methanol for 10 minutes at −20° C., washed, and stained with anti-fibronectin (F3648, 1:200 dilution) (Sigma-Aldrich) in a solution of 0.25% bovine serum albumin, 0.1% saponin, and PBS (termed BSP) at 4° C. overnight. The following day, cells were washed and incubated with secondary 594-conjugated antibody (1:200) (Jackson ImmunoResearch, West Grove, Pa.) in BSP for 1 hour at room temperature. Cells were washed and stained with SlowFade Gold reagent with DAPI (S36938) (Invitrogen, Carlsbad, Calif.) for 15 minutes and washed prior to visualization. Cells were visualized and data collected using the Cellomics High Content Screening platform (Thermo Scientific, Waltham, Mass.), Channel 2 was the object count, nuclei stained with DAPI, and channel 3 was the experimental channel count.

The inventors developed an algorithm in which the Cellomics software analyzed intensity of fibronectin staining (channel 3) within a ring 6 to 12 pixels from the nucleus for at least 5 fields per well (100 cells per image field determined by the object count in channel 2). Compounds that decreased the intensity of fibronectin staining by at least 50% below levels of the positive control (TGF-β alone) and produced a response in a dose-dependent manner were selected for further study.

An additional embodiment shown in FIG. 2 outlines the "screening" feasibility experiments performed using the high content imaging platform Cellomics. Panel A demonstrates that the Cellomics imaging platform can replicate the results observed by I.F. and in this set of experiments accurately depicting changes in fibronectin levels compared to a western blot analysis (Panel C). The mask used to measure fluorescence is depicted in Panel B. Reproducibility (Z prime score greater than 0.5) and the signal to noise was excellent (greater than 5) as depicted in panels D and E.

Using the imaging screen the inventors discovered 19 repurposed drugs (Table I) out of the 1280 present in the Prestwick library and 9 from the NIH library (Table II). Strikingly, eight of these hits were drugs belonging to the cardiac glycoside class of drugs. Dose response experiments, depicted in FIGS. 3 and 4 indicate that these hits were potent and acted at nanomolar concentrations.

Figure 3A:
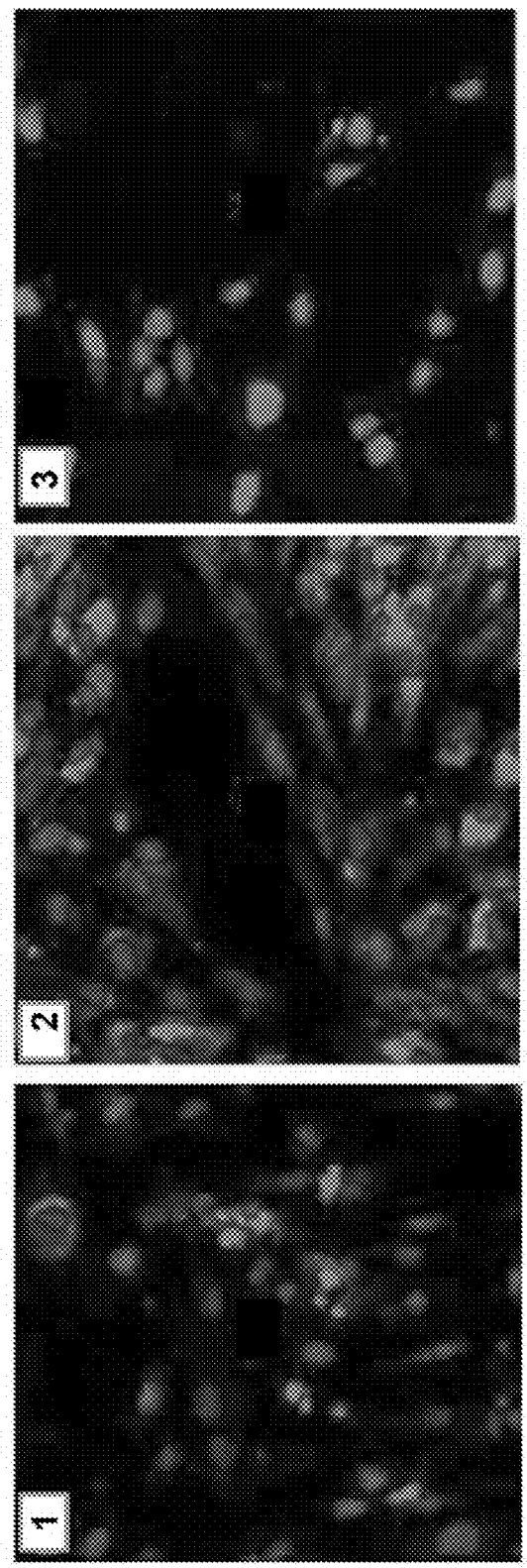
FIGS. 3A-3B: Cellomics based image analysis and western blot analysis reveal that Proscillaridin A (PsA) is a potent inhibitor of fibronectin induction although it is toxic to cells (see below). Panel A1 is the control, Panel A2 is the TGF-β treated wells and Panel A3 is TGF-β plus PsA at 5 micromolar. Images were captured using the Cellomics imaging system. Panel B is a western blot analysis indicating that PsA apparently inhibits induction of fibronectin even a low nanomolar concentrations.
Figure 3B:
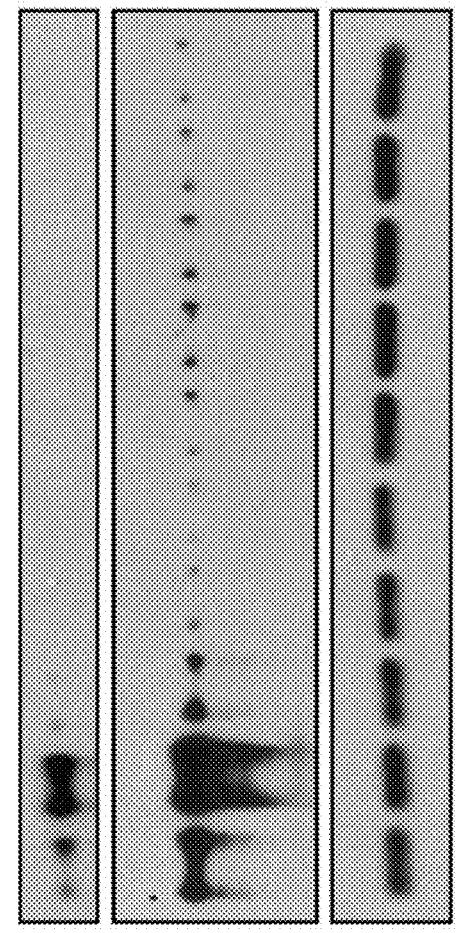
Figures 4E, 4F, 4G, 4H:
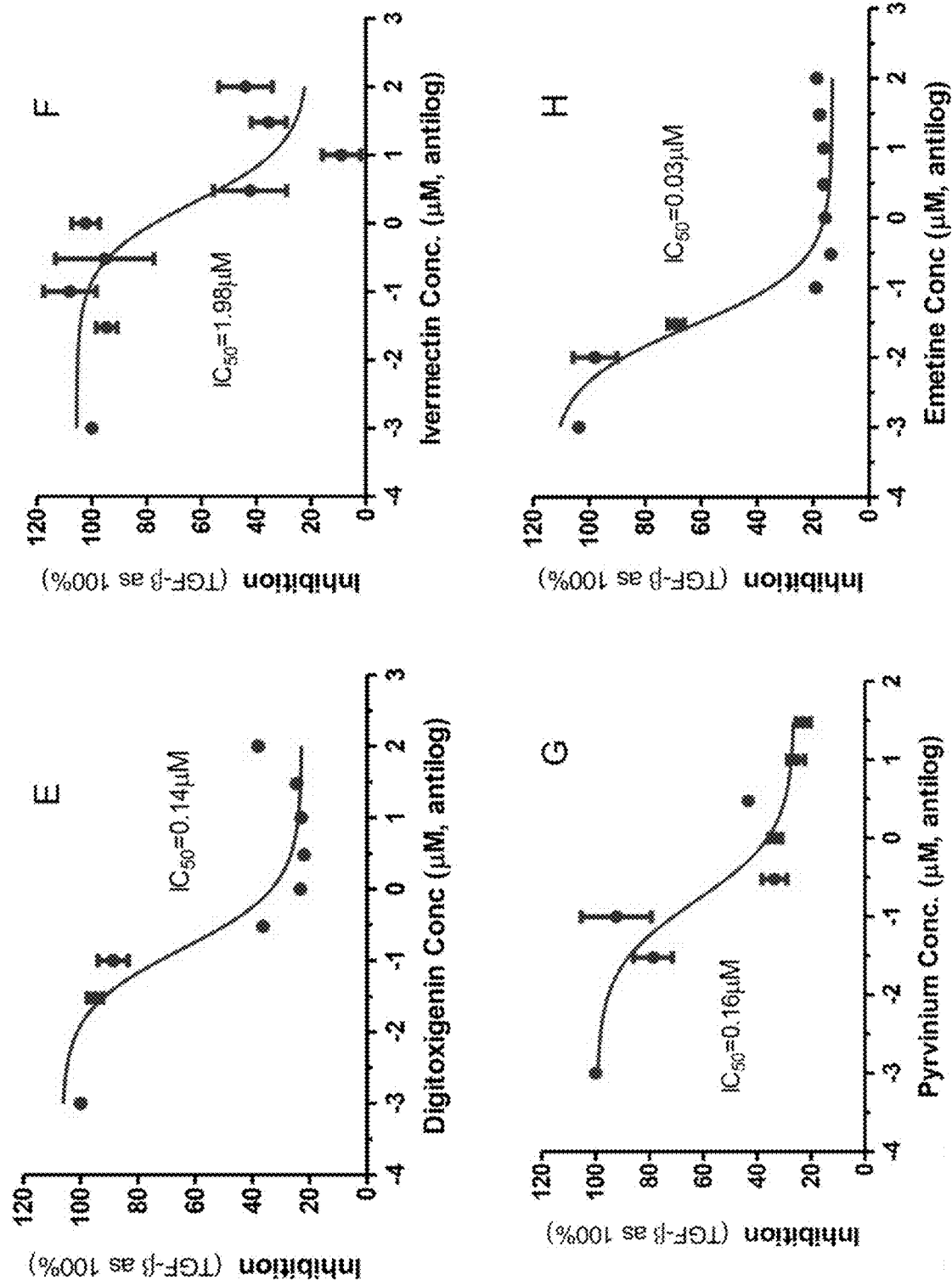
Figure 5:
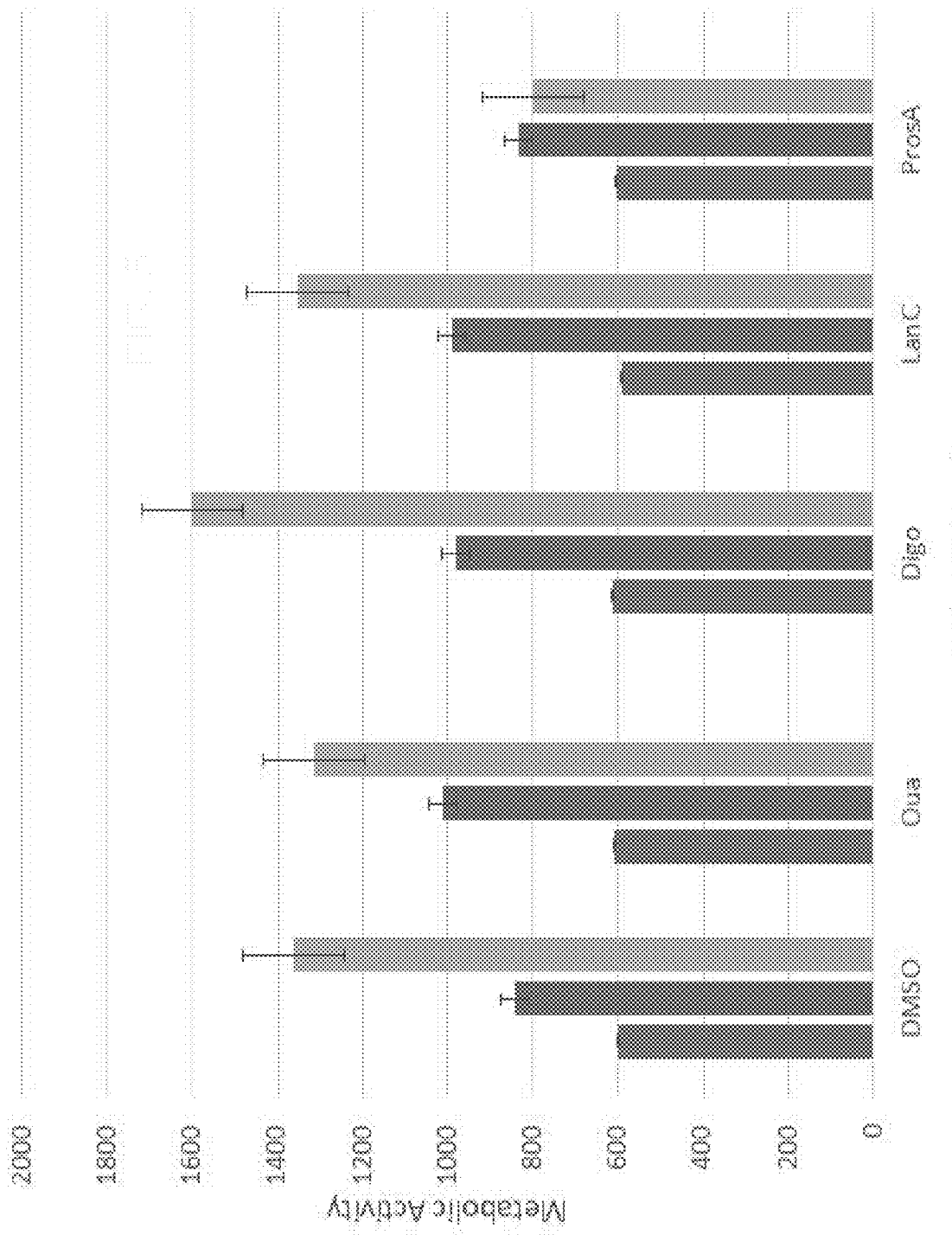
FIG. 5: Most Cardiac glycosides do not significantly decrease the metabolic activity or viability of WPMY-1 cells over a 48 hour time frame. WPMY-1 cells were treated with ouabain, digoxin, lanatoside C, or proscillaradin A at theft respective $IC_{50}$ for 0, 24, or 48 hours in 1% FBS DMEM. Metabolically viable cells (indicated by bar; left y-axis) are indicated by fluorescent intensity (560/590 nm).

Cardiac glycosides have been shown previously to inhibit cell growth in a variety of cell types, in order to determine whether cardiac glycosides inhibited TGE-β-induced fibronectin expression by affecting metabolic activity, viability assays were performed on WPMY-1 cells over 48 hours in 1% FBS DMEM. These assays were performed using the $IC_{50}$ of each respective compound, as determined above. After 48 hours, ouabain, digoxin, and lanatoside C had no effect on cell viability compared to the DMSO control. The cardiac glycoside with the lowest $IC_{50}$, proscillaridin A, caused decreased metabolic activity at 48 hours compared to the DMSO control (FIGS. 3 and 5). Therefore, the inventors focused subsequent experiments on digoxin, which has a very low $IC_{50}$ and has no effect on cell viability through 48 hours at these concentrations.

Figures 6A, 6B, 6C:
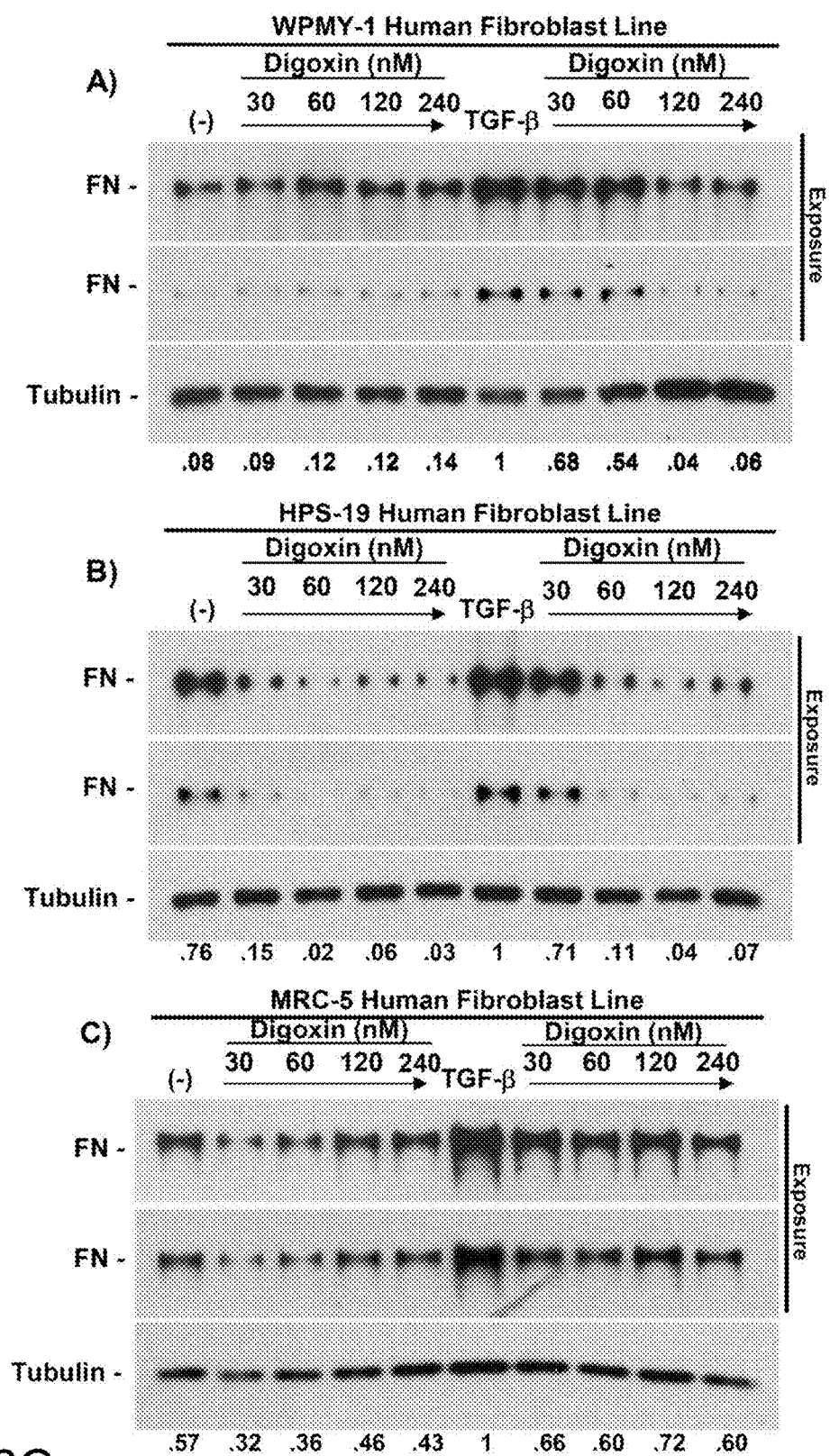
FIGS. 6A-6C: Digoxin prevents TGF-β-induced fibronectin expression in a dose dependent manner in multiple human fibroblast cell lines (A) WPMY-1 (B) HPS-19, and (C) MRC-5 human fibroblast cells were treated with or without 5 ng/ml TGF-β in the presence or absence of increasing concentrations (30, 60, 120, or 240 nM) of digoxin for 24 hours. Representative blots are shown with two exposures of fibronectin to account for strong signal intensity. n=3.

In another embodiment, the inventors found that Digoxin, in a dose response fashion, effectively inhibited induction of fibronectin in three different fibroblast cell lines as demonstrated in FIG. 6, demonstrating the effect of this drug was not just limited to one cell line.

Figures 7A, 7B, 7C, 7D:
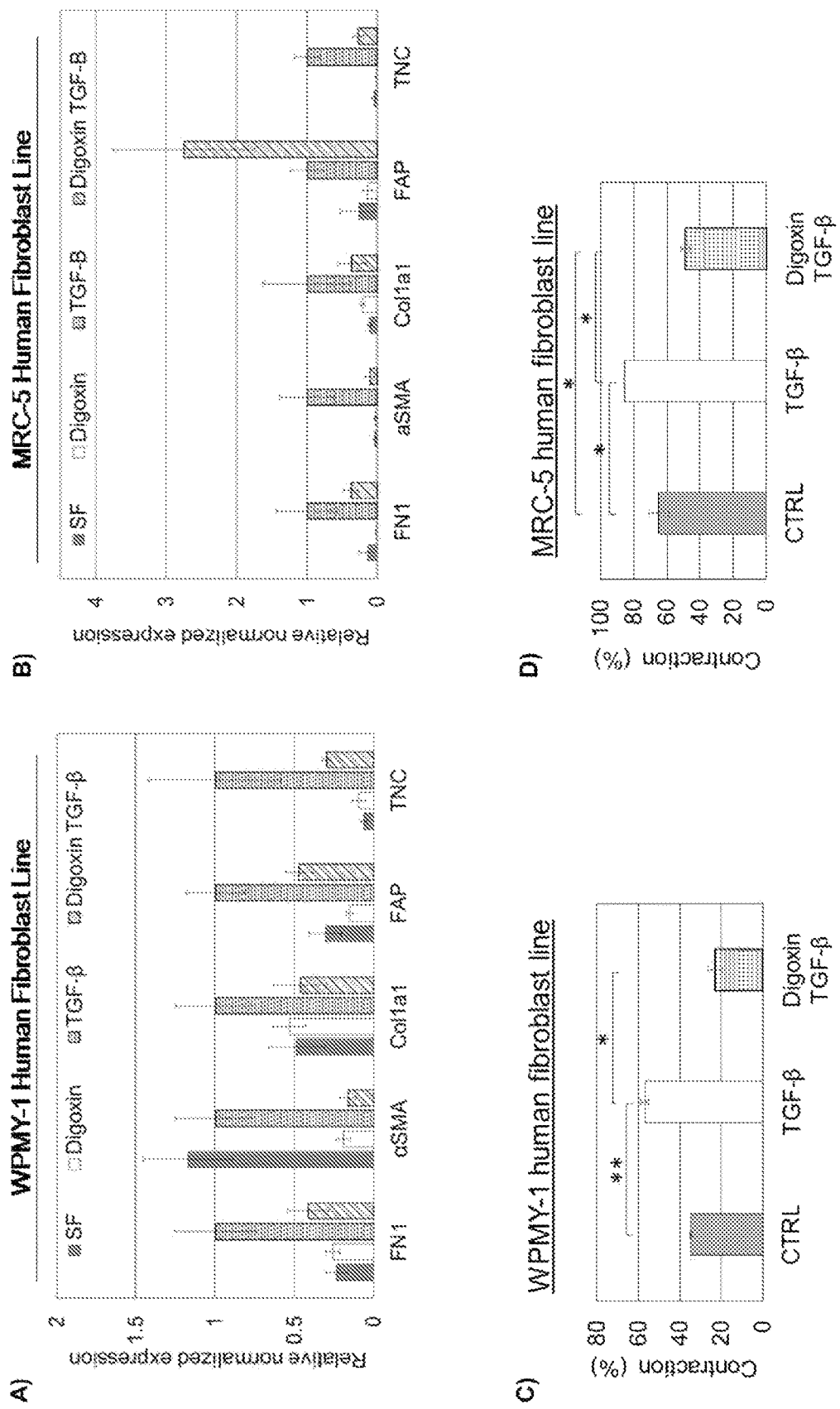
FIGS. 7A-7D: Cardiac glycosides inhibit TGF-β-induced cancer-associated fibroblast (CAF) differentiation in both WPMY-1 and MRC-5 fibroblasts. WPMY-1 (A) and MRC-5 (B) fibroblasts were treated with or without 120 nM digoxin±5 ng/ml TGF-β. RNA was isolated from cells 24 h after treatment. Real-Time PCR analysis was performed for the indicated mRNA (n=3, ±SEM). WPMY-1 (C) and MRC-5 (D) fibroblasts embedded in collagen/Matrigel were treated with or without 120 nM digoxin±5 ng/ml TGF-β for 4 days post seeding. Data are shown as percent contracted area from initial 100% well confluence. *P<0.05 and **P<0.01 indicate significant differences (n=3, Values are ±SEM).

In order to determine if digoxin prevents CAF differentiation or simply TGF-β-induced fibronectin expression, the inventors performed quantitative reverse transcriptase-PCR (qPCR) to analyze other CAF markers, including α-SMA, collagen 1a1 (COL1A1), fibroblast activation protein (FAP), and tenascin C (TNC). RNA was extracted from cells treated with 120 nM digoxin±TGF-β for 24 hours. The inventors observed that digoxin prevented TGF-β-induced expression of FN1, COL1A1, FAP, and TNC mRNA in WPMY-1 fibroblasts and FN1, α-SMA, COL1A1, and TNC in MRC-5 normal lung fibroblasts, suggesting glycosides were truly blocking the CAF differentiated phenotype (FIGS. 7A and 7B). Additionally, the inventors observed that α-SMA mRNA expression was already high in WPMY-1 cells and not increased by addition of TGF-β, but was reduced in response to digoxin treatment.

A further embodiment revealed in FIGS. 7C and 7D also indicates that digoxin inhibits TGF-β induced contraction of fibroblasts, further confirming that these drugs are blocking phenotypic differentiation of these cells as well as induction of gene expression induced by this growth factor. Contraction of the surrounding stroma by pancreatic CAFs (also called stellate cells) is one of the challenges for drugs to ultimately reach tumors from the vasculature.

Figures 8A, 8B, 8C:
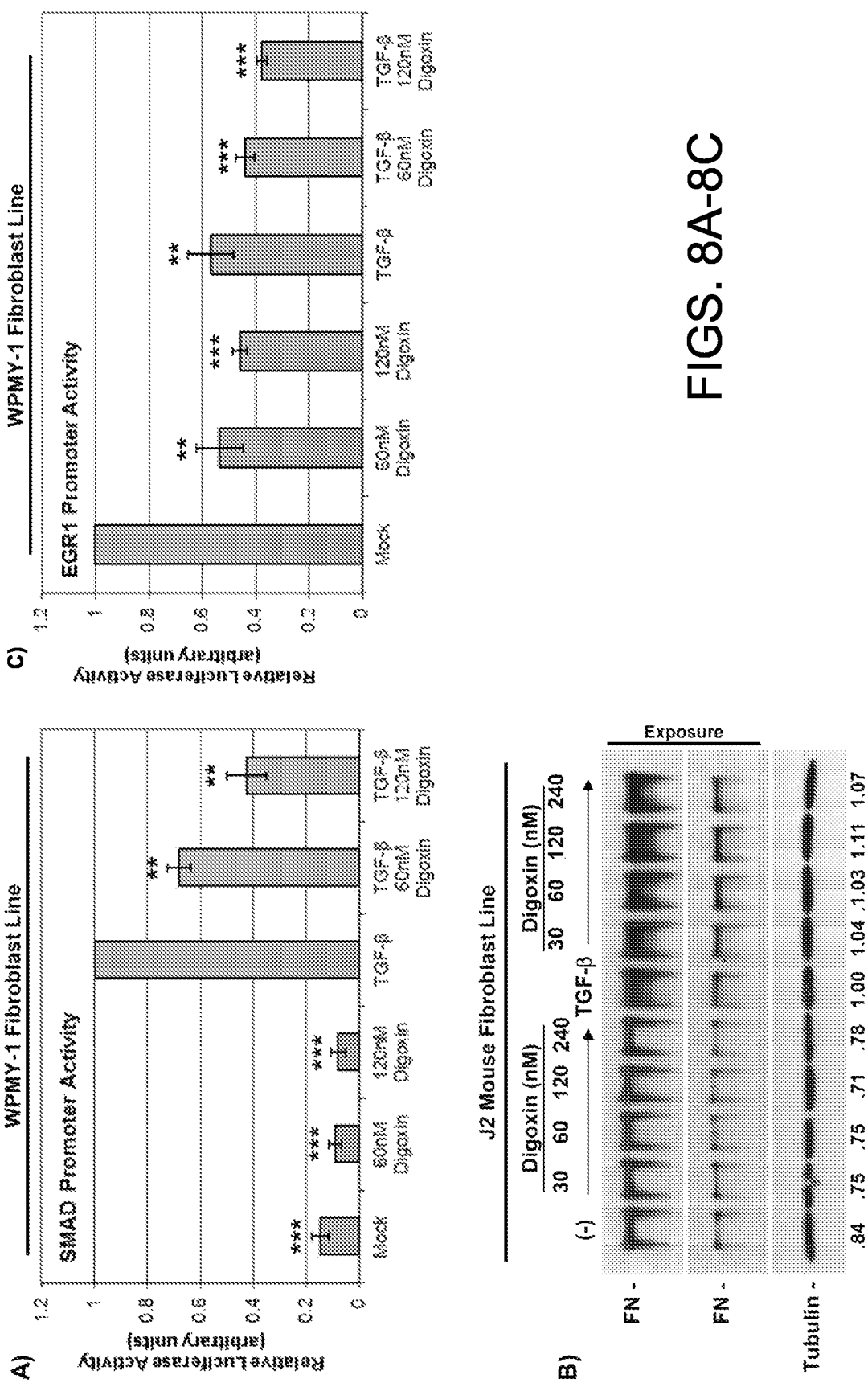
FIGS. 8A-8C: Digoxin prevents TGF-β-induced SMAD promoter activity, but does not prevent TGF-β-induced fibronectin expression in the context of the mouse Na/K ATPase. A) WPMY-1 human fibroblast cells transfected with SMAD (left) or EGR1 (right) luciferase reporter were treated with or without 5 ng/ml TGF-β in the presence or absence of Digoxin (60 or 120 nM) for 24 hours. Relative luciferase activity is shown. *P<0.05, P<0.01, *P<0.001 are significant differences compared to values set to 1 (n=3, Values are ±SEM). B) J2 mouse fibroblast cells were treated with or without 5 ng/ml TGF-β in the presence or absence of increasing concentrations (30, 60, 120, or 240 nM) of digoxin for 24 hours. Representative blot is shown with two exposures of fibronectin to account for strong signal intensity (n=3).

The embodiment presented by FIG. 8 reveals that digoxin prevents the TGF-β induction of the SMAD signaling pathway, based on a luciferase based promoter assay. Digoxin also lowers the activation of promoter dependent on EGR-1. Finally, J2 mouse fibroblast cells were treated with or without 5 ng/ml TGF-β in the presence or absence of increasing concentrations (30, 60, 120, or 240 nM) of digoxin for 24 hours. These fibroblasts do not express a form of the ATPase that is inhibited by cardiac glycosides. Digoxin did not prevent fibronectin induction even at high concentrations, suggesting that this drug is acting through its known target to block CAF differentiation ((FIG. 8B). The Y axis in these two figures uses relative units where in FIG. 8A the luciferace activity of TGF-β is set equal to 1 and in FIG. 8B the luciferace activity of mock is set equal to 1. The relative units are termed "arbitrary units" in the Figures.

This last conclusion is further supported by the embodiment demonstrated in the next series of experiments revealed in FIG. 9. Because of the observed low nanomolar effective concentration of the cardiac glycosides, the inventors hypothesized that the cardiac glycosides may be acting by binding to their high affinity target, the $Na^+/K^+$ ATPase, and that action through the ATPase is the mechanism by which the cardiac glycosides are able to block TGF-β-induced fibronectin expression. It is well documented that inhibition of the $Na^+/K^+$ ATPase by digoxin leads to increases in intracellular $Ca^{2+}$ by preventing $Ca^{2+}$ efflux through the $Na^+/Ca^{2+}$ exchanger. In order to determine if increased intracellular $Ca^{2+}$ is sufficient to prevent TGF-β-induced fibronectin expression, the inventors utilized two compounds that increase intracellular $Ca^{2+}$ concentrations. 3',4'-dichlorobenzamil hydrochloride (DCB) inhibits the $Na^+/Ca^{2+}$ exchanger, $Na^+$ transport, and sarcoplasmic reticulum $Ca^{2+}$ release channels. Thapsigargin inhibits the endoplasmic reticulum $Ca^+$ ATPase, preventing storage of $Ca^{2+}$ in the endoplasmic reticulum, causing an accumulation in the cytoplasm. Cells were treated with 2.5-10 µM of DCB or thapsigargin±TGF-β for 24 hours. The inventors found that DCB as well as thapsigargin were able to prevent TGF-β-induced fibronectin expression in a dose-dependent manner (FIGS. 9A and 9B).

Turning now to FIGS. 10A-10C, in order to determine whether pyrvinium, similar to digoxin, was able to inhibit markers of TGF-β induced Fibroblast activation, the inventors treated MRC-5 human fetal lung fibroblast cells with TGF-β and a dose escalation of either digoxin or pyrvinium. The inventors found that pyrvinium blocked the induction of fibronectin, YAP, TAZ, and smooth muscle actin by TGF-β. In furtherance of this, the inventors tested whether pyrvinium or digoxin were able to inhibit activation of fibroblasts by the combination of both TGF-β and FGF as this more accurately models a fibrotic condition driven by multiple growth factors. As with TGF-β0 alone, both digoxin and pyrvinium are able to prevent the activated fibroblast phenotype, as shown by lower levels of fibronectin, YAP, TAZ, and smooth muscle actin. To demonstrate proof-of-principle for the likely mechanism of action for pyrvinium, the inventors treated fibroblasts with verteporfin, an agent that inhibits the transcriptional co-activator function of TAZ. Pyrvinium likely functions through degradation of TAZ. Using verteporfin, the inventors demonstrate that eliminating the function of TAZ represses TGF-β induced fibronectin and smooth muscle actin expression. Of note, TAZ levels are not reduced with verteporfin whereas they are with pyrvinium treatment.

Turning next to FIGS. 11A-11F, in order to test whether digoxin and pyrvinium were able to block the induction of a activation fibroblast phenotype at the transcriptional level, the inventors performed quantitative real-time PCR. The inventors determined that digoxin and pyrvinium prevented the transcriptional induction of collagen 1a1, tenascin C, fibronectin, YAP and Snail downstream of TGF-β signaling and TAZ downstream of the fibroblast chemokine IL-8. The data also suggests digoxin and pyrvinium block this phenotype through disparate molecular mechanisms as each exhibits a more potent effect toward different transcripts—note tenascin C (TNC) versus TAZ (WWTR1v2). Together this data indicates digoxin and pyrvinium are each able to broadly repress multiple markers of the activated fibroblast phenotype, markers whose expression has pathological consequences.

Turning next to FIGS. 12A-12D, the inventors sought to determine which signaling pathways the commonly used anti-fibrotic drugs nintedanib and pirfenidone were able to inhibit in order to test whether digoxin or pyrvinium were more or equally effective. As shown in FIG. 12A, nintedanib does not bock induction by TGF-β, but blocks FGF signaling which potently upregulates TAZ in particular. In FIG. 12B, the inventors demonstrate that digoxin and pyrvinium each were able to block fibroblast activation from a combination of growth factors better than pirfenidone or nintedanib. In addition, the inventors demonstrate in FIGS. 12C and 12D that both digoxin and pyrvinium are able to block the activated fibroblast phenotype better than nintedanib upon stimulation with the combination of TGF-β and FGF. In addition, either or both of digoxin and pyrvinium can be used in combination with nintedanib and/or pirfenidone to block activation of fibroblasts.

Turning now to FIGS. 13A-13E, in a clinical setting, it would be advantageous for the efficacy of the therapeutics that the activated fibroblasts be reversed to a quiescent state upon treatment. Accordingly, the inventors tested the ability of digoxin or pyrvinium to reverse the activated fibroblast phenotype. As shown in FIG. 13A, fibroblasts pre-activated with TGF-β were chase treated with digoxin or pyrvinium alone or in combination, and were found to revert fibroblasts to the quiescent state after 24 hours of treatment as indicated by levels of fibronectin, TAZ, and smooth muscle actin. This data suggests digoxin and pyrvinium could be used to treat conditions driven by the hyperactivation of fibroblasts. The inventors further tested the potential of combination treatment with digoxin and pyrvinium at a lower range of concentrations using a more sensitive and accurate methodology. The data evidences that digoxin and pyrvinium may be used in combination to provide an additive inhibitory effect, likely through distinct mechanisms, to prevent TGF-β induced activation of fibroblasts. To test the combinations, the inventors obtained quantitative analysis of fibronectin staining in fibroblasts upon treatment with TGF-β in the presence or absence of drug combinations. Fibronectin intensity values arrayed in panel B demonstrate that particular concentrations of digoxin and pyrvinium do exhibit an effect greater in combination than alone. At relatively low concentrations of digoxin or pyrvinium alone the levels of fibronectin are reduced, but at even lower concentrations in combination the levels of fibronectin are more greatly reduced. This is likely due to each drug affecting a distinct molecular target to most completely repress the phenotype. Furthermore, the data demonstrate that digoxin and pyrvinium alone and in combination are able to repress the phenotype below even the lower basal level of activation (SF)—adding to the evidence that these drugs can revert fibroblasts to a quiescent state.

The inventors have presented experimental evidence that at least 28 drugs from at least 11 different categories of drugs/chemicals inhibit the TGB-β induction of fibronectin, a marker indicating CAF differentiation. Eight of these drugs were cardiac glycosides. Digoxin, and its related identified cardiac glycosides, apparently inhibits TGF-β-induced expression of fibronectin as well as several other markers indicative of CAF differentiation in two fibroblast cell lines. Digoxin appeared to impact SMAD and EGR1 transcriptional pathways. Digoxin inhibited a phenotypic property of fibroblasts, namely contraction. This inhibition was seen at low nanomolar concentrations, which have minimal effects on cell viability in vitro through 48 hours. Because of the low concentrations that were required for inhibition, it is unlikely that off-target effects are responsible for the observed phenotype. Further experiments evidence that inhibition of the Na$^+$/K$^+$ ATPase, the known target of cardiac glycosides, is able to prevent TGF-β-induced CAF differentiation.

Fibronectin was chosen as the key marker of CAF differentiation for several reasons. Fibronectin is an extracellular matrix protein that binds receptor proteins called integrins and plays a role in wound healing, migration, and growth of cells during development. In cancer, this leads to increased tumor invasion and metastasis. Additionally, fibronectin is over-expressed in non-cancerous fibrotic diseases such as pulmonary fibrosis, cystic fibrosis, and cirrhosis. Finally, fibronectin shows the most significant upregulation of the CAF markers in response to TGF-β. These factors make fibronectin an attractive target for inhibition and for screens to discover drugs that block CAF formation, both in the context of cancer and fibrotic diseases.

Inhibition of the Na$^+$/K$^+$ ATPase causes increased levels of cytosolic Na$^+$, which can no longer be pumped out of the cell. This indirectly blocks the Na$^+$/Ca$^{2+}$ exchanger, leading to elevated intracellular Ca$^{2+}$. The inventors found that two drugs which increase cytosolic Ca$^{2+}$, dichlorobenzamil (DCB) and thapsigargin, were able also able to inhibit TGF-β-induced fibronectin expression. DCB and thapsigargin work through a different mechanism from digoxin to increase cytosolic Ca$^{2+}$ levels. BAPTA-AM (Glycine, N,N'-[1,2-ethanediylbis(oxy-2,1-phenylene)]bis[N-[2-[(acetyloxy)methyl]-2-oxoethyl]]-, bis[(acetyloxy)methyl] ester), a Ca$^{2+}$ chelator, had no effect on TGF-β-induced fibronectin expression. These results are consistent with the mechanism that an increase in cytosolic Ca$^{2+}$ through inhibition of the Na$^+$/K$^+$ ATPase can prevent TGF-β-induced fibronectin expression, and open up additional pathways to inhibit CAF differentiation.

The inventors are aware of a calcium ion channel receptor called transient receptor potential cation channel subfamily M member 8 (TRPM8) that exists on fibroblasts. Activation of this receptor increases intracellular calcium. Therefore, based on the results above, the inventors conclude that the following chemicals that activate the TRPM8 receptor would inhibit CAF formations: menthol, linalool (3,7-dimethylocta-1,6-dien-3-ol), geraniol ((trans)-3,7-Dimethyl-2,6-octadien-1-ol), hydroxy-citronellal (7-hydroxy-3,7-dimethyloctanal), WS-3 (N-ethyl-5-methyl-2-propan-2-ylcyclohexane-1-carboxamide), WS-23 (N,2,3-trimethyl-2-propan-2-ylbutanamide), Frescolat MGA (9-methyl-6-propan-2-yl-1,4-dioxaspiro[4.5]decan-2-yl)methanol), Frescolat ML ([(1R,2S,5R)-5-methyl-2-propan-2-ylcyclohexyl] 2-hydroxypropanoate), PMD 38 (2-(1-Hydroxy-1-methylethyl)-5-methylcyclohexanol), Coolact P ((1R,2R,5S)-5-methyl-2-prop-1-en-2-ylcyclohexan-1-ol), Cooling Agent 10 (3-(I-Menthoxy)propane-1,2-diol) and rotundifolone ((1S,6S)-6-methyl-3-propan-2-ylidene-7-oxabicyclo[4.1.0]heptan-2-one).

The inventors used 3T3-J2 murine fibroblasts, which are highly resistant to cardiac glycosides compared to theft human counterpart. The inventors found that digoxin did not have an effect on TGF-β-induced fibronectin expression in murine fibroblasts. These results suggest that digoxin does function by targeting the Na$^+$/K$^+$ ATPase.

Mechanistically, digoxin appears to be inhibiting CAF differentiation at the level of transcription. Analysis of mRNA levels by qPCR showed that TGF-β increases the transcript levels of CAF differentiation markers and that this increase is abrogated by the addition of digoxin. Examination of the promoter regions showed that each of the CAF differentiation markers has a binding site for the TGF-β-regulated transcription factors Smad2/3 and EGR1, both of which are expressed in WPMY-1 fibroblasts. Calcium-sensing receptor (CaSR) has been shown to negatively regulate Smad2 phosphorylation in response to calcium. The inventors' data evidences that digoxin prevents activity of the transcription factors Smad2/3. Smad2/3 is part of a transcription factor complex that is activated in response to TGF-β signaling. Signaling through the TGF-β receptor induces phosphorylation of Smad2 and Smad3, which are free to translocate to the nucleus and form complexes with Smad4. This complex binds to promoters that regulate proliferation, apoptosis, or differentiation, depending on the cellular context.

Digoxin is approved by the FDA and indicated for the treatment of congestive heart failure, atrial fibrillation, and atrial flutters. These effects were dependent on the Na$^+$/K$^+$ ATPase. There is no previous report of the efficacy of digoxin and other cardiac in preventing the differentiation of fibroblasts to CAFs. The ability of digoxin to prevent growth factor induced fibronectin expression evidences that these compounds will be able to counteract an established disease state driven by an activated myofibroblast or CAF phenotype. Based on the above data, a pharmacologically effective dose of digoxin for a human would preferably be 0.1 to 5 mg/kg, more preferably be 0.5 to 2.5 mg/kg, and most preferably be 1.0 to 2.0 mg/kg.

In conclusion, the inventors have provided evidence that digoxin and other cardiac glycosides are effective in preventing CAF differentiation. Nine other "hits" remain to be tested for their mechanism of action. Mechanistically, digoxin prevents fibroblast activation through modulation cytosolic Ca$^{2+}$ levels which leads to a decrease in the transcription of several markers of CAF differentiation. The inventors evidence that digoxin/cardiac glycosides as well as the other non-cardiac glycoside drugs and other drugs and drug classes listed in Tables 1 and 2 are beneficial in combination with each other and/or with other anti-tumor agents, thus targeting the tumor epithelia as well as preventing and reversing the activation of CAFs in the tumor microenvironment. Effective combinations of these agents or these agents with the standard of care used in pancreatic cancer (gemcitabine and/or Nab-paclitaxel) could enter clinical trials fairly rapidly since the drugs involved are already FDA approved. This combination would represent a first in class. Further, the evidence suggests that these drugs and drug categories listed in Tables 1 and 2, alone or in combination with each other and/or with other anti-fibrosis drugs will be effective against a wide panoply of activated fibrosis associated diseases and pre-disease conditions.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

We claim:

1. A method of ameliorating an activated fibroblast associated disease in a mammal, in need thereof, comprising administering a pharmaceutical composition comprising a therapeutically effective amount of pyrvinium, or a pharmacologically acceptable salt thereof, wherein
the activated fibroblast associated disease is selected from the group consisting of pulmonary fibrosis, idiopathic pulmonary fibrosis, nonalcoholic steatohepatitis, renal fibrosis, scleroderma/systemic sclerosis.

2. The method of claim 1, wherein the activated fibroblast associated disease is pulmonary fibrosis.

3. The method of claim 1, wherein the pharmacologically acceptable salt of pyrvinium is prepared with a variable counter anion, the variable counter ion being one of a halide, tosylate, triflate and pamoate.

4. The method of claim 1, wherein the pharmacologically acceptable salt of pyrvinium is prepared with phosphate.

5. A method of ameliorating an activated fibroblast associated disease in a mammal, in need thereof, comprising administering a pharmaceutical composition comprising a therapeutically effective amount of a combination of pyrvinium, or a pharmacologically acceptable salt thereof, and digoxin: wherein the therapeutically effective amount of pyrvinium and/or digoxin, when used in combination, is lower than would be required to be therapeutically effective when pyrvinium or digoxin, is administered alone: further wherein the activated fibroblast associated disease is selected from the group consisting of fibrosis, pulmonary fibrosis, idiopathic pulmonary fibrosis, radiation-induced lung injury, non-alcoholic fatty liver disease, nonalcoholic steatohepatitis, cirrhosis, hepatocellular carcinoma, cardiac fibrosis, atrial fibrosis, endomyocardial fibrosis, old myocardial fibrosis, glial scarring (gliosis), renal fibrosis, pancreatic cancer, arthrofibrosis, crohn's disease, dupuytren's contracture, myofibroblastic tumors, mediastinal fibrosis, retroperitoneal cavity fibrosis, myelofibrosis, keloid/skin fibrosis, pyronie's disease, nephrogenic systemic fibrosis, progressive massive fibrosis, retroperitoneal fibrosis, scleroderma/systemic sclerosis, adhesive capsulitis and cancers with solid tumors.

6. The method of claim 5, wherein the pharmacologically acceptable salt of pyrvinium is prepared with a variable counter anion, the variable counter ion being one of a halide, tosylate, triflate and pamoate.

7. The method of claim 5, wherein the activated fibroblast associated disease is pulmonary fibrosis, idiopathic pulmonary fibrosis, nonalcoholic steatohepatitis, renal fibrosis, or scleroderma/systemic sclerosis.

8. The method of claim 5, wherein the activated fibroblast associated disease is pulmonary fibrosis.

* * * * *